(12) United States Patent
Meerpoel et al.

(10) Patent No.: US 9,637,490 B2
(45) Date of Patent: May 2, 2017

(54) ANTIFUNGAL 5,6-DIHYDRO-4-[(DIFLUOROETHYL)PHENYL]-4H-PYRROLO[1,2-α][1,4]BENZODIAZEPINE AND 4-(DIFLUOROETHYL)PHENYL-6H-PYRROLO[1,2-α][1,4]BENZODIAZEPINE DERIVATIVES

(75) Inventors: Lieven Meerpoel, Beerse (BE); Louis Jules Roger Marie Maes, Lille (BE); Kelly de Wit, Merksem (BE)

(73) Assignee: Janssen Pharmaceutica NV, Beerse (BE)

( * ) Notice: Subject to any disclaimer, the term of this patent is extended or adjusted under 35 U.S.C. 154(b) by 1032 days.

(21) Appl. No.: 13/702,361

(22) PCT Filed: Jun. 1, 2011

(86) PCT No.: PCT/EP2011/059058
§ 371 (c)(1),
(2), (4) Date: Dec. 6, 2012

(87) PCT Pub. No.: WO2011/154298
PCT Pub. Date: Dec. 15, 2011

(65) Prior Publication Data
US 2013/0085136 A1 Apr. 4, 2013

(30) Foreign Application Priority Data
Jun. 7, 2010 (EP) ..................... 10165076

(51) Int. Cl.
C07D 487/12 (2006.01)
A61K 31/55 (2006.01)
C07D 487/04 (2006.01)

(52) U.S. Cl.
CPC ................. *C07D 487/04* (2013.01)

(58) Field of Classification Search
None
See application file for complete search history.

(56) References Cited

FOREIGN PATENT DOCUMENTS

WO    WO 02/34752    5/2002

OTHER PUBLICATIONS

Cheeseman et al., J. Heterocyclic Chem., 241-244, 1979.
Cheeseman et al., Journal of the Chemical Society, pp. 2732-2734 (1971).
Meerpoel et al., Bioorganic & Medicinal Chemistry Letters, vol. 15, No. 14, pp. 3453-3458, (2005).
Raines et al., Journal of Heterocyclic Chemistry, vol. 13, No. 4, pp. 711-716 (1976).
Trinka et al., J. Prakt. Chem., 338, 675-678 (1996).

*Primary Examiner* — Jeffrey S Lundgren
*Assistant Examiner* — Michael Schmitt
(74) *Attorney, Agent, or Firm* — Thomas J. Dodd

(57) ABSTRACT

The present invention concerns novel compounds of Formula (I):

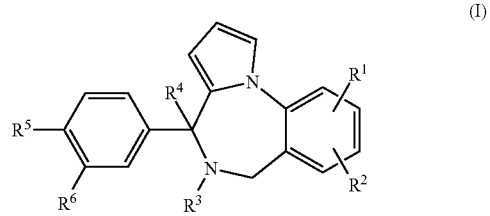

wherein $R^1$, $R^2$, $R^3$, $R^4$, $R^5$ and $R^6$ have the meaning defined in the claims. The compounds according to the present invention are active mainly against dermatophytes and systemic fungal infections. The invention further relates to processes for preparing such novel compounds, pharmaceutical compositions comprising said compounds as an active ingredient as well as the use of said compounds as a medicament.

13 Claims, No Drawings

ANTIFUNGAL 5,6-DIHYDRO-4-[(DIFLUOROETHYL)PHENYL]-4H-PYRROLO[1,2-α][1,4]BENZODIAZEPINE AND 4-(DIFLUOROETHYL)PHENYL-6H-PYRROLO[1,2-α][1,4]BENZODIAZEPINE DERIVATIVES

CROSS REFERENCE TO RELATED APPLICATIONS

This application is a national stage application of Patent Application No. PCT/EP2011/059058, filed Jun. 1, 2011, which in turn claims the benefit of EPO Patent Application No. EPO/10165076.0 filed Jun. 7, 2010. The complete disclosures of the aforementioned related patent applications are hereby incorporated herein by reference for all purposes.

FIELD OF THE INVENTION

The present invention is concerned with novel antifungal 5,6-dihydro-4-[(difluoro-ethyl)phenyl]-4H-pyrrolo[1,2-a][1,4]benzodiazepine and 4-(difluoroethyl)phenyl-6H-pyrrolo[1,2-a][1,4]benzodiazepine derivatives, active mainly against dermatophytes and systemic fungal infections. The invention further relates to processes for preparing such novel compounds, pharmaceutical compositions comprising said compounds as an active ingredient as well as the use of said compounds as a medicament.

BACKGROUND OF THE INVENTION

Dermatophyte is a common label for a group of 3 types of fungi that commonly causes skin disease in animals and humans. These anamorphic (asexual or imperfect fungi) genera are: *Microsporum, Epidermophyton* and *Trichophyton*. There are about 40 species in these 3 genera.

Dermatophytes cause infections of the skin, hair and nails due to their ability to obtain nutrients from keratinized material. The organisms colonize the keratin tissues and inflammation is caused by host response to metabolic by-products. They are usually restricted to the cornified layer of the epidermis because of their inability to penetrate viable tissue of an immunocompetent host. However, occasionally the organisms do invade subcutaneous tissues, resulting in kerion development. Invasion does elicit a host response ranging from mild to severe. Acid proteinases, elastase, keratinases, and other proteinases reportedly act as virulence factors.

Systemic fungal infections (SFI) are life-threatening conditions that most commonly affect patients with reduced immunity often resulting from therapeutic interventions to treat malignant diseases. The number of SFI's in modern hospitals keeps increasing, and the number of different fungi that have been involved in SFI is large and still growing. Despite many cases of invasive candidiasis and aspergillosis there has been an increased incidence of infections due to other molds like *Scedosporium apiospermum, Fusarium* spp., and *Zygomycetes, Rhizopus* and *Mucor* spp. Effective therapeutic agents treating all these infections very well therefore need to have very broad spectrum of activity. In the past few decades itraconazole, fluconazole, ketoconazole, and intravenous or liposomal amphotericin B have been used in SFI, and all of these agents have their limitations with regard to spectrum, safety or ease of administration. More recently a third generation of azoles have been investigated and introduced to the market, improving the treatment options in intensive care units. Voriconazole (Vfend™) and posaconazole (Noxafil™) show much improvement of treatment towards life threatening invasive SFI such as candidiasis, aspergillosis, and infections due to *Fusarium* species at clinical relevant dosages. Moreover posaconazole shows efficacy against infections caused by the emerging *Zygomycetes* spp. Echinocandins, such as anidulafungin, caspofungin, and micafungin, which are non-competitive inhibitors of 1,3-β-glucan synthesis in fungal cell walls, display high efficacy against *Candida* spp. and *Aspergillus* spp., but no activity against *Cryptococcus, Fusarium,* or *Zygomycetes* spp. Of all antimycotic agents, azoles still represent a unique class of compounds displaying the broadest antifungal spectrum via inhibition of 14-α-demethylase, an enzyme being essential for ergosterol biosynthesis in fungi.

Onychomycosis is the most common disease of the nails and constitutes about a half of all nail abnormalities. The prevalence of onychomycosis is about 6-8% in the adult population. The causative pathogens of onychomycosis include dermatophytes, *Candida*, and non-dermatophytic moulds. Dermatophytes are the fungi most commonly responsible for onychomycosis in the temperate western countries; meanwhile, *Candida* and non-dermatophytic moulds are more frequently involved in the tropics and subtropics. *Trichophyton rubrum* is the most common dermathophyte involved in onychomycosis. Other dermatophytes that may be involved are *Trichophyton interdigitale, Epidermophyton floccosum, Trichophyton violaceum, Microsporum gypseum, Trichophyton tonsurans, Trichophyton soudanense* and *Trichophyton verrucosum*. Other causative pathogens include *Candida* and non-dermatophytic moulds, in particular members of the mould generation *Scytalidium* (also *Neoscytalidium*), *Scopulariopsis*, and *Aspergillus*.

5,6-Dihydro-4H-pyrrolo[1,2-a][1,4]benzodiazepines have been described in J. Chem. Soc.(C), 2732-2734 (1971); J. Heterocyclic Chem., 13, 711-716 (1976); and J. Heterocyclic Chem., 16, 241-244 (1979). The compounds disclosed in these references all have a different substitution on the phenyl moiety in the 4-position and moreover no biological activities were reported in any of these references.

WO02/34752 describes 4-substituted 5,6-dihydro-4H-pyrrolo[1,2-a][1,4]benzo-diazepines as a new class of antifungal compounds. However, WO02/34752 does not specifically disclose the present substitution pattern on the phenyl moiety in the 4-position.

Many drug compounds, while possessing desired therapeutic properties, are used inefficiently due to their poor water solubility. Thus for example, where such compounds are administered orally, only a small fraction of the drug is taken up into the blood during transit of the gastro-intestinal tract. As a result, to achieve adequate drug uptake it may be necessary to administer high doses of the drug compound, to prolong the period of drug administration or to make frequent administrations of the drug compound. Indeed, the poor solubility and hence poor bioavailability of a drug may cause an alternative drug, perhaps one with undesired side effects or one which requires invasive administration (e.g. by injection or infusion), to be used in place of the poorly soluble drug.

Therefore it is an object of the present invention to produce more bioavailable compounds with a broad antifungal spectrum or to provide useful alternative compounds, maintaining adequately high therapeutic efficacy and adequately low toxicity or other side effects.

Unexpectedly, the antifungal compounds of the present invention or part of the compounds of the present invention may have improved metabolic stability properties, improved PK (pharmacokinetic) properties, improved solubilities, reduced cytochrome P450 liabilities, or improved bioavailability compared with the compounds disclosed in the prior art.

The compounds of the present invention are useful as squalene epoxidase inhibitors.

It is accordingly an object of the present invention to provide novel compounds with antifungal activity to overcome or ameliorate at least one of the disadvantages of the prior art, or to provide a useful alternative.

SUMMARY OF THE INVENTION

It has been found that the compounds of the present invention are useful as antifungal compounds.

The present invention concerns novel compounds of Formula (I):

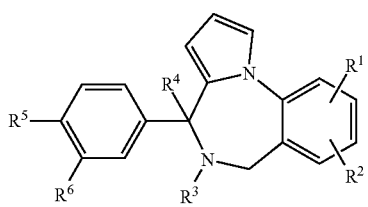

(I)

and stereoisomeric forms thereof, wherein
$R^1$ is hydrogen, chloro or fluoro;
$R^2$ is hydrogen, chloro, fluoro or methyl;
$R^3$ and $R^4$ are hydrogen;
or $R^3$ and $R^4$ taken together form a bond;
$R^5$ is 1,1-difluoroethyl, and $R^6$ is hydrogen or fluoro;
or $R^5$ is hydrogen or fluoro, and $R^6$ is 1,1-difluoroethyl;
and the pharmaceutically acceptable addition salts, and the solvates thereof.

The present invention also concerns methods for the preparation of compounds of Formula (I) and pharmaceutical compositions comprising them.

The present compounds are useful agents for combating fungi in vivo.

The novel compounds described in the present invention may be useful in the treatment or prevention of infections caused by dermatophytes, systemic fungal infections and onychomycosis.

The novel compounds described in the present invention may be active against a wide variety of fungi, such as *Candida* spp., e.g. *Candida albicans, Candida glabrata, Candida kruceï, Candida parapsilosis, Candida kefyr, Candida tropicalis; Aspergillus* spp., e.g. *Aspergillus fumigatus, Aspergillus niger, Aspergillus flavus; Cryptococcus neoformans; Sporothrix schenckii; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus; Mucor circinelloides; Rhizopus* spp., e.g. *Rhizopus oryzae, Rhizopus microspores; Malassezia furfur; Acremonium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces.*

In view of the aforementioned pharmacology of the present compounds, it follows that they are suitable for use as a medicament.

The invention also relates to a compound according to the general Formula (I), the stereoisomeric forms thereof and the pharmaceutically acceptable addition salts and the solvates thereof, for use in the treatment or prevention of fungal infections.

One advantage of the compounds or a part of the compounds of the present invention may lie in their enhanced bioavailability, improved metabolic stability properties, improved PK properties, reduced hERG channel inhibition, or reduced cytochrome P450 liabilities compared with the compounds disclosed in the prior art.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

In case of tautomeric forms, it should be clear that the other non-depicted tautomeric form is also included within the scope of the present invention.

The atoms in the tricyclic system are numbered as shown in the following formula (XX):

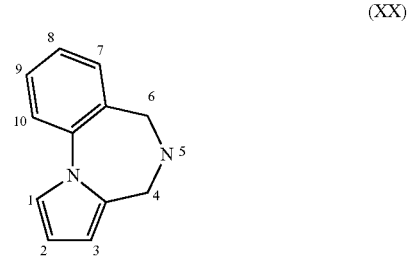 [SMILES: c1ccc2c(c1)CNCc1cccn1-2]

(XX)

It will be appreciated that some of the compounds of Formula (I) and their pharmaceutically acceptable addition salts and solvates may contain one or more centers of chirality and exist as stereoisomeric forms.

Hereinbefore and hereinafter, the term "compound of formula (I)" is meant to include the addition salts, the solvates and the stereoisomers thereof.

The terms "stereoisomers", "stereoisomeric forms" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

The present invention concerns novel compounds of Formula (I):

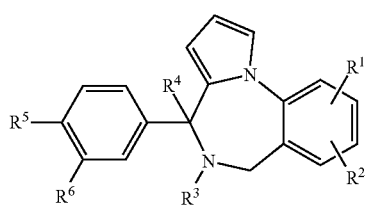

and stereoisomeric forms thereof, wherein
$R^1$ is hydrogen, chloro or fluoro;
$R^2$ is hydrogen, chloro, fluoro or methyl;
$R^3$ and $R^4$ are hydrogen;
or $R^3$ and $R^4$ taken together form a bond;
$R^5$ is 1,1-difluoroethyl, and $R^6$ is hydrogen or fluoro;
or $R^5$ is hydrogen or fluoro, and $R^6$ is 1,1-difluoroethyl;
and the pharmaceutically acceptable addition salts, and the solvates thereof.

In an embodiment, the invention relates to compounds of Formula (I) and stereoisomeric forms thereof, wherein
$R^1$ is chloro or fluoro;
$R^2$ is hydrogen, chloro, fluoro or methyl;
$R^3$ and $R^4$ are hydrogen;
or $R^3$ and $R^4$ taken together form a bond;
$R^5$ is 1,1-difluoroethyl, and $R^6$ is hydrogen or fluoro;
or $R^5$ is hydrogen or fluoro, and $R^6$ is 1,1-difluoroethyl;
and the pharmaceutically acceptable addition salts, and the solvates thereof.

In an embodiment, the invention relates to compounds of Formula (I) and stereoisomeric forms thereof, wherein
$R^1$ is chloro or fluoro;
$R^2$ is chloro, fluoro or methyl;
$R^3$ and $R^4$ are hydrogen;
or $R^3$ and $R^4$ taken together form a bond;
$R^5$ is 1,1-difluoroethyl, and $R^6$ is hydrogen or fluoro;
or $R^5$ is hydrogen or fluoro, and $R^6$ is 1,1-difluoroethyl;
and the pharmaceutically acceptable addition salts, and the solvates thereof.

In an embodiment, the invention relates to compounds of Formula (I) and stereoisomeric forms thereof, wherein
$R^1$ is chloro or fluoro;
$R^2$ is hydrogen, chloro, fluoro or methyl;
$R^3$ and $R^4$ are taken together to form a bond;
$R^5$ is 1,1-difluoroethyl, and $R^6$ is hydrogen or fluoro;
or $R^5$ is hydrogen or fluoro, and $R^6$ is 1,1-difluoroethyl;
and the pharmaceutically acceptable addition salts, and the solvates thereof.

In another embodiment, the invention relates to compounds of Formula (I) and stereoisomeric forms thereof, wherein
$R^1$ is chloro or fluoro;
$R^2$ is hydrogen;
$R^3$ and $R^4$ taken together form a bond;
$R^5$ is 1,1-difluoroethyl;
$R^6$ is hydrogen;
and the pharmaceutically acceptable addition salts, and the solvates thereof.

In a next embodiment, the invention relates to any of the other embodiments or any combination of the other embodiments, wherein $R^5$ is 1,1-difluoroethyl and $R^6$ is hydrogen or fluoro.

In a further embodiment, the invention relates to any of the other embodiments or any combination of the other embodiments, wherein $R^5$ is hydrogen or fluoro and $R^6$ is 1,1-difluoroethyl.

In a next embodiment, the invention relates to any of the other embodiments or any combination of the other embodiments, wherein at least one of $R^1$ and $R^2$ is other than hydrogen.

In a particular embodiment, the invention relates to any of the other embodiments or any combination of the other embodiments, wherein $R^2$ is hydrogen, chloro or fluoro.

In another embodiment, the invention relates to any of the other embodiments or any combination of the other embodiments, wherein $R^3$ and $R^4$ are hydrogen.

In another embodiment, the invention relates to any of the other embodiments or any combination of the other embodiments, wherein $R^1$ or $R^2$ is in the 7-position and is other than hydrogen.

In another embodiment, the invention relates to any of the other embodiments or any combination of the other embodiments, wherein $R^1$ is in the 7-position and is chloro or fluoro; in particular $R^1$ is in the 7-position and is chloro.

In another embodiment, the invention relates to any of the other embodiments or any combination of the other embodiments, wherein
$R^1$ is in the 7-position and is chloro or fluoro; in particular $R^1$ is in the 7-position and is chloro; and
$R^2$ is in any of the other positions and is hydrogen, chloro, fluoro or methyl; in particular chloro, fluoro or methyl; more in particular chloro or fluoro; even more in particular chloro.

In another embodiment, the invention relates to any of the other embodiments or any combination of the other embodiments, wherein $R^2$ is in the 7-position and is chloro, fluoro or methyl.

In another embodiment, the invention relates to any of the other embodiments or any combination of the other embodiments, wherein
$R^2$ is in the 7-position and is chloro, fluoro or methyl; and
$R^1$ is in any of the other positions and is hydrogen, chloro or fluoro; in particular chloro or fluoro; more in particular chloro.

In a further embodiment, the invention relates to any of the other embodiments or any combination of the other embodiments, wherein $R^3$ and $R^4$ are taken together to form a bond.

In a next embodiment the compound of Formula (I) is selected from the group comprising:
7-chloro-4-[4-(1,1-difluoroethyl)phenyl]-5,6-dihydro-4H-pyrrolo[1,2-a][1,4]-benzodiazepine,
7-chloro-4-[4-(1,1-difluoroethyl)phenyl]-5,6-dihydro-4H-pyrrolo[1,2-a][1,4]-benzodiazepine.HCl,
(4S)-7-chloro-4-[4-(1,1-difluoroethyl)phenyl]-5,6-dihydro-4H-pyrrolo[1,2-a][1,4]-benzodiazepine,
(4S)-7-chloro-4-[4-(1,1-difluoroethyl)phenyl]-5,6-dihydro-4H-pyrrolo[1,2-a][1,4]-benzodiazepine.HCl,
(4R)-7-chloro-4-[4-(1,1-difluoroethyl)phenyl]-5,6-dihydro-4H-pyrrolo[1,2-a][1,4]-benzodiazepine,
(4R)-7-chloro-4-[4-(1,1-difluoroethyl)phenyl]-5,6-dihydro-4H-pyrrolo[1,2-a][1,4]-benzodiazepine.HCl,
8,10-dichloro-4-[4-(1,1-difluoroethyl)phenyl]-5,6-dihydro-4H-pyrrolo[1,2-a][1,4]-benzodiazepine, 8,10-dichloro-4-[4-(1,1-difluoroethyl)phenyl]-5,6-dihydro-4H-pyrrolo[1,2-a][1,4]-benzodiazepine.HCl,
8,10-dichloro-4-[4-(1,1-difluoroethyl)phenyl]-6H-pyrrolo[1,2-a][1,4]benzodiazepine,
7,8-dichloro-4-[4-(1,1-difluoroethyl)phenyl]-5,6-dihydro-4H-pyrrolo[1,2-a][1,4]-benzodiazepine,
7,8-dichloro-4-[4-(1,1-difluoroethyl)phenyl]-5,6-dihydro-4H-pyrrolo[1,2-a][1,4]-benzodiazepine.HCl,
7,10-dichloro-4-[4-(1,1-difluoroethyl)phenyl]-6H-pyrrolo[1,2-a][1,4]benzodiazepine,
7,9-dichloro-4-[4-(1,1-difluoroethyl)phenyl]-6H-pyrrolo[1,2-a][1,4]benzodiazepine,
7,8-dichloro-4-[4-(1,1-difluoroethyl)phenyl]-6H-pyrrolo[1,2-a][1,4]benzodiazepine,
7,10-dichloro-4-[4-(1,1-difluoroethyl)phenyl]-5,6-dihydro-4H-pyrrolo[1,2-a][1,4]-benzodiazepine,
7,10-dichloro-4-[4-(1,1-difluoroethyl)phenyl]-5,6-dihydro-4H-pyrrolo[1,2-a][1,4]-benzodiazepine.HCl,
7,9-dichloro-4-[4-(1,1-difluoroethyl)phenyl]-5,6-dihydro-4H-pyrrolo[1,2-a][1,4]-benzodiazepine,
7,9-dichloro-4-[4-(1,1-difluoroethyl)phenyl]-5,6-dihydro-4H-pyrrolo[1,2-a][1,4]-benzodiazepine.HCl,
7-chloro-4-[4-(1,1-difluoroethyl)phenyl]-6H-pyrrolo[1,2-a][1,4]benzodiazepine,
7-chloro-4-[3-(1,1-difluoroethyl)phenyl]-6H-pyrrolo[1,2-a][1,4]benzodiazepine,
4-[4-(1,1-difluoroethyl)phenyl]-7-fluoro-6H-pyrrolo[1,2-a][1,4]benzodiazepine,
9-chloro-4-[4-(1,1-difluoroethyl)phenyl]-7-methyl-6H-pyrrolo[1,2-a][1,4]-benzodiazepine,
9-chloro-4-[4-(1,1-difluoroethyl)phenyl]-6H-pyrrolo[1,2-a][1,4]benzodiazepine,
4-[4-(1,1-difluoroethyl)phenyl]-7,9-difluoro-6H-pyrrolo[1,2-a][1,4]benzodiazepine,
10-chloro-4-[4-(1,1-difluoroethyl)phenyl]-6H-pyrrolo[1,2-a][1,4]benzodiazepine,
4-[3-(1,1-difluoroethyl)-4-fluorophenyl]-7-fluoro-6H-pyrrolo[1,2-a][1,4]benzodiazepine,
7-chloro-4-[3-(1,1-difluoroethyl)-4-fluorophenyl]-6H-pyrrolo[1,2-a][1,4]benzodiazepine,
9,10-dichloro-4-[4-(1,1-difluoroethyl)phenyl]-6H-pyrrolo[1,2-a][1,4]benzodiazepine,
4-[3-(1,1-difluoroethyl)-4-fluorophenyl]-7,9-difluoro-6H-pyrrolo[1,2-a][1,4]-benzodiazepine,
7-chloro-4-[4-(1,1-difluoroethyl)phenyl]-9-fluoro-5,6-dihydro-4H-pyrrolo[1,2-a][1,4]-benzodiazepine,
7-chloro-4-[4-(1,1-difluoroethyl)phenyl]-9-fluoro-5,6-dihydro-4H-pyrrolo[1,2-a][1,4]-benzodiazepine.HCl,
7,9-dichloro-4-[3-(1,1-difluoroethyl)-4-fluorophenyl]-6H-pyrrolo[1,2-a][1,4]-benzodiazepine,
7-chloro-4-[3-(1,1-difluoroethyl)-4-fluorophenyl]-9-fluoro-6H-pyrrolo[1,2-a][1,4]-benzodiazepine,
7-chloro-4-[4-(1,1-difluoroethyl)phenyl]-9-fluoro-6H-pyrrolo[1,2-a][1,4]benzodiazepine,
10-chloro-4-[4-(1,1-difluoroethyl)phenyl]-7-methyl-6H-pyrrolo[1,2-a][1,4]-benzodiazepine,
7-chloro-4-[3-(1,1-difluoroethyl)phenyl]-5,6-dihydro-4H-pyrrolo[1,2-a][1,4]-benzodiazepine,
7-chloro-4-[3-(1,1-difluoroethyl)phenyl]-5,6-dihydro-4H-pyrrolo[1,2-a][1,4]-benzodiazepine.HCl,
7-chloro-4-[4-(1,1-difluoroethyl)-3-fluorophenyl]-6H-pyrrolo[1,2-a][1,4]benzodiazepine,
4-[4-(1,1-difluoroethyl)-3-fluorophenyl]-7-fluoro-6H-pyrrolo[1,2-a][1,4]benzodiazepine,
7-chloro-4-[4-(1,1-difluoroethyl)-3-fluorophenyl]-9-fluoro-6H-pyrrolo[1,2-a][1,4]-benzodiazepine,
9-chloro-4-[4-(1,1-difluoroethyl)phenyl]-7-fluoro-6H-pyrrolo[1,2-a][1,4]benzodiazepine,
4-[4-(1,1-difluoroethyl)-3-fluorophenyl]-7,9-difluoro-6H-pyrrolo[1,2-a][1,4]-benzodiazepine,
9-chloro-4-[3-(1,1-difluoroethyl)-4-fluorophenyl]-6H-pyrrolo[1,2-a][1,4]benzodiazepine,
10-chloro-4-[3-(1,1-difluoroethyl)-4-fluorophenyl]-6H-pyrrolo[1,2-a][1,4]-benzodiazepine,
including any stereochemically isomeric form thereof, and the pharmaceutically acceptable addition salts and the solvates thereof.

In an even other embodiment the compound of Formula (I) is 7-chloro-4-[4-(1,1-difluoroethyl)phenyl]-6H-pyrrolo[1,2-a][1,4]benzodiazepine.

All possible combinations of the above-indicated interesting embodiments are considered to be embraced within the scope of this invention.

The present invention also encompasses processes for the preparation of compounds of Formula (I) and subgroups thereof The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The compounds of the present invention can be prepared according to Scheme 1:

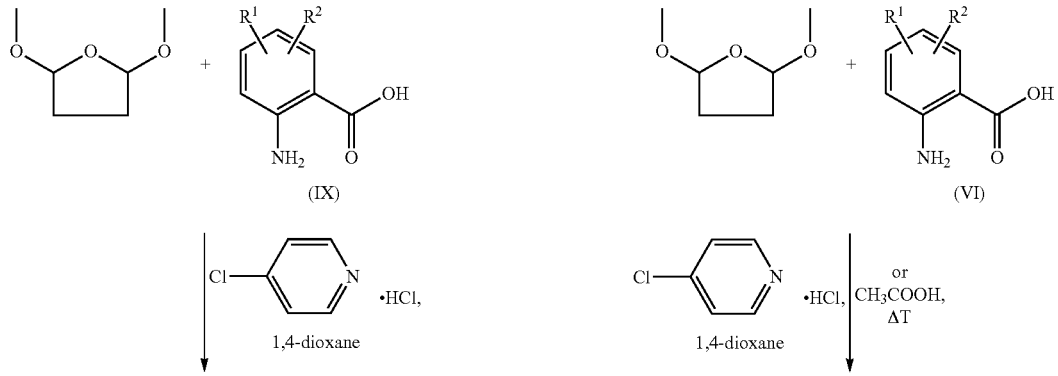

Scheme 1

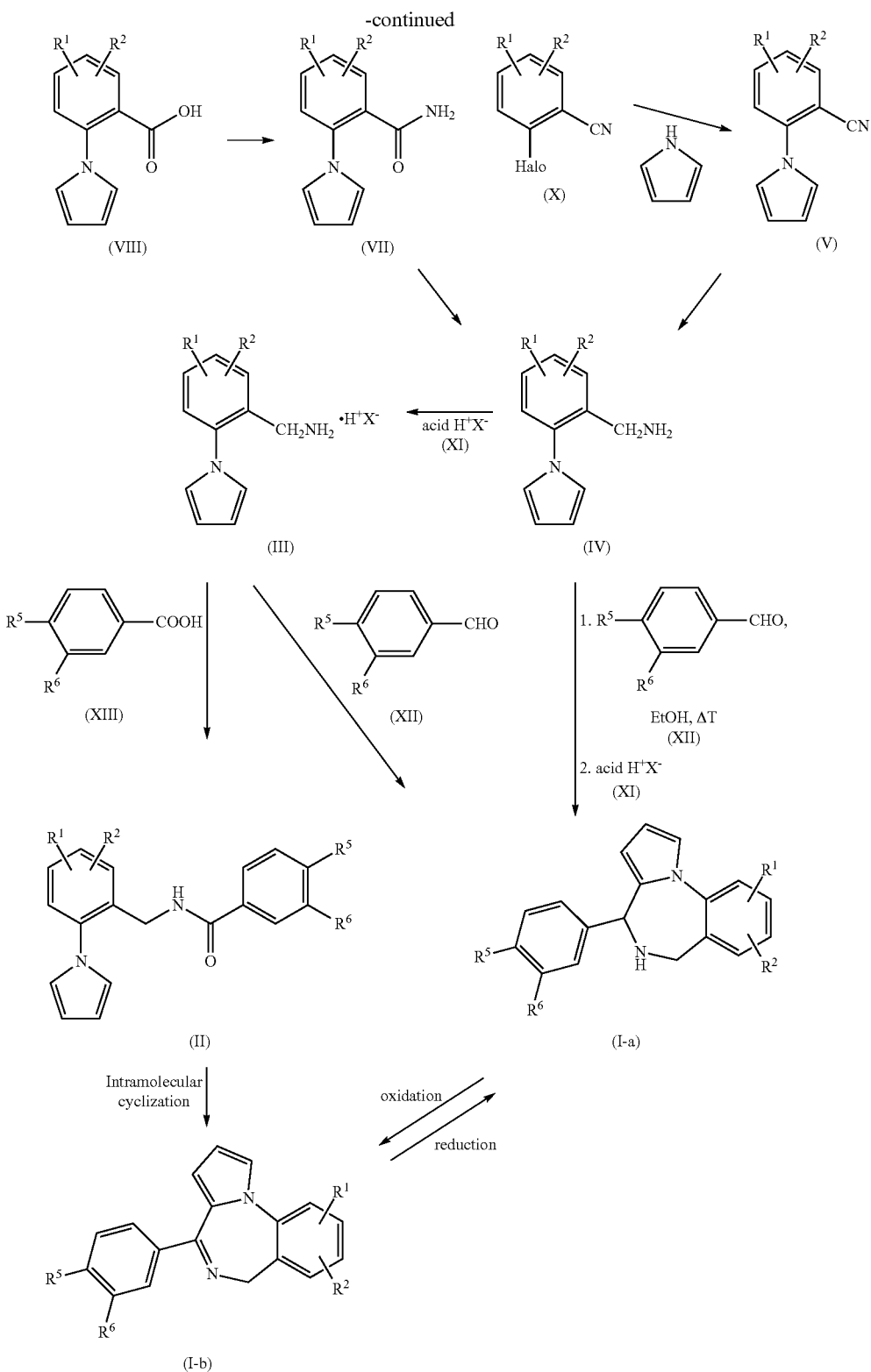

The compounds of Formula (I) wherein $R^3$ and $R^4$ together form an extra bond, said compounds being represented by formula (I-b), can be prepared from the compounds represented by the formula (I-a), following art-known amine to imine oxidation reactions. These oxidation reactions may be conducted by reacting a compound of formula (I-a) with an oxidant such as, for example, lead tetra-acetate or manganese dioxide, in a reaction inert solvent such as a halogenated hydrocarbon e.g. dichloromethane (DCM) or trichloromethane. The reaction rate can be enhanced by stirring and optionally heating the reaction mixture.

Alternatively, a compound of formula (I-b) can be prepared by an intramolecular cyclization of an intermediate of formula (II). In the presence of an acid such as, for example, POCl$_3$, the amide in the intermediate of formula (II) can function as a C-electrophile, resulting in a ring closure. The reaction may be performed in a suitable solvents such as, for example, DCM. Stirring and heating may enhance the rate of the reaction.

A compound of formula (I-a) can be prepared from an intermediate of formula (IV) by converting it in a salt (III) by reaction with an acid H$^+$X$^-$ of formula (XI), and reacting said salt of formula (III) with an aldehyde of formula (XII) in an appropriate solvent such as an alcohol, e.g. methanol (MeOH), ethanol (EtOH), isopropanol, at an elevated temperature, preferably at reflux temperature.

Alternatively, the intermediate of formula (IV) may be reacted first with the aldehyde of formula (XII) and the thus formed imine may be cyclized in the presence of an acid H$^+$X$^-$ of formula (XI) to a compound of formula (I-a).

Alternatively, a compound of formula (I-a) may be obtained by the reduction of a compound of formula (I-b) by using methods well-known to those skilled in the art.

An intermediate of formula (II) may be prepared by a coupling reaction between an intermediate of formula (III) and (XIII). Said reaction may be performed in the presence of coupling agents such as typically 1-hydroxy-1H-benzotriazole (HOBt) and N'-(ethylcarbonimidoyl)-N,N-dimethyl-1,3-propanediamine monohydrochloride (EDCI). The reaction may be performed in the presence of a base such as trietylamine (Et$_3$N) and a suitable solvent such as, for example, DCM. Alternatively, an acid chloride derivative of (XIII) or a reactive ester derivative of (XIII) can also be used in this type of reaction to prepare an intermediate of formula (II).

An intermediate of formula (XIII) or its acid chloride or ester derivative, can be easily prepared by those skilled in the art.

Intermediates of formula (III) and (IV) are prepared by reducing a 1-(2-cyano-phenyl)pyrrole derivative of formula (V). Several procedures well-known to those skilled in the art may be used to reduce the nitrile function such as, for example:

1. LiAlH$_4$/THF [S. Raines, S. Y. Chai and F. P. Palopoli; J. Heterocyclic Chem., 13, 711-716 (1976)]
2. i. sodium bis(2-methoxyethoxy)aluminate (Red-Al®) 70% w/w Toluene, RT: ii. NaOH 10%, RT [G. W. H. Cheeseman and S. G. Greenberg; J. Heterocyclic Chem., 16, 241-244 (1979)]
3a. i. KBH$_4$/CF$_3$COOH, THF; ii. H$_2$O; iii. HCl[P. Trinka, P. Slégel and J. Reiter; J. Prakt. Chem., 338, 675-678 (1996)]
3b. Borane-dimethyl sulfide (1:1), THF
4a. RaNi (Raney Nickel)/H$_2$
4b. RaNi/thiophene solution/(MeOH/NH$_3$)

Even other well-known methods for reducing the nitrile function may also be used.

An intermediate of formula (V) in turn is commercially available or alternatively can be easily prepared by, for example, treating a 2-aminobenzonitrile derivative of formula (VI) with tetrahydro-2,5-dimethoxyfuran in an inert solvent such as dioxane or tetrahydrofuran (THF) in the presence of an acid such as 4-chloropyridine hydrochloride, or in an acidic solvent such as glacial acetic acid, at an elevated temperature, preferably at reflux temperature. Alternatively, an intermediate of formula (V) can also be prepared from an intermediate of formula (X). Typically, an intermediate of formula (X) wherein Halo is defined as Br, I, Cl or F, is reacted with pyrrole in the presence of a base such as, for example, Cs$_2$CO$_3$ or NaH, in a suitable solvent such as typically DMF.

Alternatively, an intermediate of formula (IV) may be prepared by treating an intermediate of formula (VII) with borane-dimethyl sulfide (1:1) in a suitable solvent such as, for example, THF. The reaction typically can be performed in the presence of an acid such as HCl. After the reaction has proceeded, the reaction mixture can be basified with a suitable base such as NaOH. The reaction can be performed at an elevated temperature, preferably at reflux temperature.

An intermediate of formula (VII) can be prepared from an intermediate of formula (VIII). An intermediate of formula (VIII) can be reacted with a nitrogen source such as, NH$_3$.H$_2$O in the presence of HOBt and EDCI. This type of reaction typically can be performed in a suitable solvent like DMF. Stirring of the reaction mixture may enhance the rate of reaction.

An intermediate of formula (VIII) can be easily prepared by treating an intermediate of formula (IX) with tetrahydro-2,5-dimethoxyfuran in an inert solvent such as dioxane in the presence of an acid such as 4-chloropyridine hydrochloride at an elevated temperature, preferably at reflux temperature. Alternatively, a reactive ester derivative of (IX) can also be used in this type of reaction to prepare an intermediate of formula (VIII).

All starting materials are commercially available or can be easily prepared by those skilled in the art.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethylphenyl carbamate) or Chiralpak® AS, both purchased from Daicel Chemical Industries, Ltd, in Japan.

Pure stereoisomeric forms of the compounds and the intermediates of this invention may be obtained by the application of art-known procedures. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of Formula (I) are obviously intended to be included within the scope of the invention.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

The compounds of Formula (I) and stereoisomeric forms thereof, and the pharmaceutically acceptable addition salts, and the solvates thereof, may be active against dimorphic pathogens, dermatophytes, zygomycetes, hyaline hyphomycetes, dematiaceous hyphomycetes, yeasts and yeastlike organisms.

The compounds of Formula (I) and stereoisomeric forms thereof, and the pharmaceutically acceptable addition salts, and the solvates thereof, may be active against dimorphic pathogens, yeasts and yeastlike organisms.

The compounds of Formula (I) and stereoisomeric forms thereof, and the pharmaceutically acceptable addition salts, and the solvates thereof, may be active against moulds.

The compounds of Formula (I) and stereoisomeric forms thereof, and the pharmaceutically acceptable addition salts, and the solvates thereof, may be active against a wide variety of fungi, such as *Candida* spp., e.g. *Candida albicans, Candida glabrata, Candida kruceï; Candida parapsilosis, Candida kefyr, Candida tropicalis; Aspergillus* spp., e.g. *Aspergillus fumigatus, Aspergillus niger, Aspergillus flavus; Cryptococcus neoformans; Sporothrix schenckii; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus; Mucor circinelloides; Rhizopus* spp., e.g. *Rhizopus oryzae, Rhizopus microspores; Malassezia furfur; Acremonium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces.*

The compounds of Formula (I) and stereoisomeric forms thereof, and the pharmaceutically acceptable addition salts, and the solvates thereof, may be active against a wide variety of fungi, such as *Candida parapsilosis; Aspergillus* spp., e.g. *Aspergillus fumigatus, Aspergillus niger, Aspergillus flavus; Cryptococcus neoformans; Sporothrix schenckii; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor*spp., e.g. *Rhizomucor miehei, Rhizomucor pusillus; Mucor circinelloides; Rhizopus* spp., e.g. *Rhizopus oryzae, Rhizopus microspores; Acremonium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces.*

The compounds of Formula (I) and stereoisomeric forms thereof, and the pharmaceutically acceptable addition salts, and the solvates thereof, may be active against a wide variety of fungi, such as *Candida parapsilosis; Aspergillus* spp., e.g. *Aspergillus fumigatus, Aspergillus niger, Aspergillus flavus; Cryptococcus neoformans; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus; Mucor circinelloides; Rhizopus* spp., e.g. *Rhizopus oryzae, Rhizopus microspores; Acre-monium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces*; in particular *Aspergillus* spp., e.g. *Aspergillus fumigatus, Aspergillus niger, Aspergillus flavus; Cryptococcus neoformans; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus; Mucor circinelloides; Rhizopus* spp., e.g. *Rhizopus oryzae, Rhizopus microspores; Acremonium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces.*

The compounds of Formula (I) and stereoisomeric forms thereof, and the pharmaceutically acceptable addition salts, and the solvates thereof, may be active against *Candida parapsilosis* B66126, *Aspergillus fumigatus* B42928, *Cryptococcus neoformans* B66663, *Sporothrix schenckii* B62482, *Microsporum canis* B68128, *Trichophyton mentagrophytes* B70554, *Trichophyton rubrum* B68183, *Scedosporium apiospermum* IHEM3817 and *Scedosporium prolificans* IHEM21157.

The compounds of Formula (I) and stereoisomeric forms thereof, and the pharmaceutically acceptable addition salts, and the solvates thereof, may be active against *Candida parapsilosis* B66126, *Aspergillus fumigatus* B42928, *Cryptococcus neoformans* B66663, *Sporothrix schenckii* B62482, *Microsporum canis* B68128, *Trichophyton mentagrophytes* B70554, *Trichophyton rubrum* B68183, *Scedosporium apiospermum* IHEM3817, *Scedosporium prolificans* IHEM21157, *Rhizopus oryzae* IHEM5223, *Rhizomucor miehei* IHEM13391 and *Mucor circinelloides* IHEM21105.

The compounds of Formula (I) and stereoisomeric forms thereof, and the pharmaceutically acceptable addition salts, and the solvates thereof, may be active against *Candida parapsilosis, Aspergillus fumigatus, Cryptococcus neoformans, Sporothrix schenckii, Microsporum canis, Trichophyton mentagrophytes, Trichophyton rubrum, Scedosporium apiospermum, Scedosporium prolificans, Rhizopus oryzae, Rhizomucor miehei* and *Mucor circinelloides.*

The compounds of Formula (I) and stereoisomeric forms thereof, and the pharmaceutically acceptable addition salts, and the solvates thereof, may be active against *Candida parapsilosis, Aspergillus fumigatus, Cryptococcus neoformans, Sporothrix schenckii, Microsporum canis, Trichophyton mentagrophytes, Trichophyton rubrum, Scedosporium apiospermum* and *Scedosporium prolificans*; in particular *Aspergillus fumigatus, Microsporum canis, Trichophyton mentagrophytes, Trichophyton rubrum, Scedosporium apiospermum* and *Scedosporium prolificans.*

The compounds of Formula (I) and stereoisomeric forms thereof, and the pharmaceutically acceptable addition salts, and the solvates thereof, may be active against a wide variety of fungi, such as *Candida parapsilosis; Aspergillus* spp.; *Cryptococcus neoformans; Sporothrix schenckii; Microsporum* spp.; *Fusarium* spp.; *Scedosporium* spp.;

in particular *Candida parapsilosis*; *Aspergillus* spp.; *Cryptococcus neoformans*; *Microsporum* spp.; *Fusarium* spp.; *Scedosporium* spp.;

more in particular *Aspergillus* spp.; *Cryptococcus neoformans*; *Microsporum* spp.; *Fusarium* spp.; *Scedosporium* spp.

The compounds of Formula (I) and stereoisomeric forms thereof, and the pharmaceutically acceptable addition salts, and the solvates thereof, may be active against a wide variety of fungi, such as *Candida parapsilosis*; *Aspergillus* spp.; *Cryptococcus neoformans*; *Trichophyton* spp.; *Sporothrix schenckii*; *Microsporum* spp.; *Fusarium* spp.; *Scedosporium* spp.;

in particular *Aspergillus* spp.; *Microsporum* spp.; *Trichophyton* spp.

The compounds of Formula (I) and stereoisomeric forms thereof, and the pharmaceutically acceptable addition salts, and the solvates thereof, may be active against fungi such as *Candida parapsilosis*; *Aspergillus* spp., e.g. *Aspergillus fumigatus*, *Aspergillus niger*, *Aspergillus flavus*; *Cryptococcus neoformans*; *Sporothrix schenckii*; *Epidermophyton floccosum*; *Microsporum canis*; *Trichophyton* spp., e.g. *Trichophyton mentagrophytes*, *Trichophyton rubrum*, *Trichophyton quinckeanum*;

in particular *Candida parapsilosis*; *Aspergillus* spp., e.g. *Aspergillus fumigatus*, *Aspergillus niger*, *Aspergillus flavus*; *Cryptococcus neoformans*; *Epidermophyton floccosum*; *Microsporum canis*; *Trichophyton* spp., e.g. *Trichophyton mentagrophytes*, *Trichophyton rubrum*, *Trichophyton quinckeanum*;

more in particular *Aspergillus* spp., e.g. *Aspergillus fumigatus*, *Aspergillus niger*, *Aspergillus flavus*; *Cryptococcus neoformans*; *Epidermophyton floccosum*; *Microsporum canis*; *Trichophyton* spp., e.g. *Trichophyton mentagrophytes*, *Trichophyton rubrum*, *Trichophyton quinckeanum*.

The compounds of Formula (I) and stereoisomeric forms thereof, and the pharmaceutically acceptable addition salts, and the solvates thereof, may be active against fungi such as *Candida parapsilosis*; *Aspergillus* spp.; *Cryptococcus neoformans*; *Microsporum* spp.; *Trichophyton* spp.; *Scedosporium* spp.

The compounds of Formula (I) and stereoisomeric forms thereof, and the pharmaceutically acceptable addition salts, and the solvates thereof, may be active against *Candida parapsilosis*, *Aspergillus fumigatus*, *Cryptococcus neoformans*, *Sporothrix schenckii*, *Microsporum canis*, *Trichophyton mentagrophytes*, *Trichophyton rubrum*, *Scedosporium apiospermum* and *Scedosporium prolificans*;

in particular *Candida parapsilosis*, *Aspergillus fumigatus*, *Cryptococcus neoformans*, *Microsporum canis*, *Trichophyton mentagrophytes*, *Trichophyton rubrum*, *Scedosporium apiospermum* and *Scedosporium prolificans*;

more in particular *Aspergillus fumigatus*, *Cryptococcus neoformans*, *Microsporum canis*, *Trichophyton mentagrophytes*, *Trichophyton rubrum*, *Scedosporium apiospermum* and *Scedosporium prolificans*.

The compounds of Formula (I) and stereoisomeric forms thereof, and the pharmaceutically acceptable addition salts, and the solvates thereof, may be active against a variety of fungi that infect the skin, hair and nails, as well as subcutaneous and systemic fungal pathogens.

The compounds of Formula (I) and stereoisomeric forms thereof, and the pharmaceutically acceptable addition salts, and the solvates thereof, may be active against the 3 dermatophyte genera: *Trichophyton*, *Microsporum* and *Epidermophyton*; in particular against *Trichophyton* and *Microsporum*.

The compounds of Formula (I) and stereoisomeric forms thereof, and the pharmaceutically acceptable addition salts, and the solvates thereof, may be active against dermatophytes and *Aspergillus* spp.; in particular *Microsporum canis*, *Trichophyton mentagrophytes*, *Trichophyton rubrum* and *Aspergillus fumigatus*; more in particular *Microsporum canis*, *Trichophyton mentagrophytes* and *Trichophyton rubrum*.

The compounds of Formula (I) and stereoisomeric forms thereof, and the pharmaceutically acceptable addition salts, and the solvates thereof, may be active against *Trichophyton mentagrophytes*, *Trichophyton rubrum* and *Aspergillus* spp.; in particular *Trichophyton mentagrophytes*, *Trichophyton rubrum* and *Aspergillus fumigatus*.

The compounds of Formula (I) and stereoisomeric forms thereof, and the pharmaceutically acceptable addition salts, and the solvates thereof, may be active against *Trichophyton mentagrophytes*; *Trichophyton rubrum*; *Aspergillus* spp., e.g. *Aspergillus fumigatus*; *Fusarium* spp.; *Mucor* Spp.; *Zygomycetes* spp.; *Scedosporium* spp.; *Microsporum canis*; *Sporothrix schenckii*; *Cryptococcus neoformans* and *Candida parapsilosis*.

The compounds of Formula (I) and stereoisomeric forms thereof, and the pharmaceutically acceptable addition salts, and the solvates thereof, may be active against dermatophytes.

The compounds of Formula (I) and stereoisomeric forms thereof, and the pharmaceutically acceptable addition salts, and the solvates thereof, may be active against *Aspergillus fumigatus*.

The compounds of Formula (I) and stereoisomeric forms thereof, and the pharmaceutically acceptable addition salts, and the solvates thereof, may be active against a wide variety of fungi, such as one or more of the fungi mentioned hereinbefore.

The compounds of Formula (I) and stereoisomeric forms thereof, and the pharmaceutically acceptable addition salts, and the solvates thereof, are potent antifungals when administered orally or topically.

The compounds of the present invention may be useful as ergosterol synthesis inhibitors.

In view of the utility of the compound of Formula (I), there is provided a method of treating warm-blooded animals, including humans, suffering from, or a method of preventing warm-blooded animals, including humans, to suffer from any one of the diseases mentioned hereinbefore. Hence, compounds of Formula (I) are provided for use as a medicine. Also the use of a compound of Formula (I) in the manufacture of a medicament useful in treating fungal infections is provided. Further compounds of Formula (I) are provided for use in the treatment of fungal infections.

As used herein, the term "treatment" is intended to refer to all processes, wherein there may be a slowing, interrupting, arresting, or stopping of the progression of an infection, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for the treatment of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention, in particular treatment, of fungal infections; in particular fungal infections caused by one or more of the fungi selected from a group consisting of fungi mentioned hereinbefore.

The invention also relates to a compound according to the general Formula (I), the stereoisomeric forms thereof and the pharmaceutically acceptable acid or base addition salts and the solvates thereof, for use in the treatment of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of a fungal infection, in particular a fungal infection caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of a fungal infection, wherein the fungal infection is caused by one or more of the fungi selected from the group consisting of *Candida* spp.; *Aspergillus* spp.; *Cryptococcus neoformans*; *Sporothrix schenckii*; *Epidermophyton floccosum*; *Microsporum* spp.; *Trichophyton* spp; *Fusarium* spp.; *Rhizomucor* spp.; *Mucor circinelloides*; *Rhizopus* spp.; *Malassezia furfur*; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*;
in particular wherein the fungal infection is caused by one or more of the fungi selected from the group consisting of *Candida parapsdosis*; *Aspergillus* spp.; *Cryptococcus neoformans*; *Sporothrix schenckii*; *Epidermophyton floccosum*; *Microsporum* spp.; *Trichophyton* spp.; *Fusarium* spp.; *Rhizomucor* spp.; *Mucor circinelloides*; *Rhizopus* spp.; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*;
even more in particular wherein the fungal infection is caused by one or more of the fungi selected from the group consisting of *Microsporum canis, Trichophyton mentagrophytes, Trichophyton rubrum* and *Aspergillus fumigatus*.

The novel compounds described in the present invention may be useful in the treatment or prevention of diseases or conditions selected from the group consisting of infections caused by dermatophytes, systemic fungal infections and onychomycosis.

The novel compounds described in the present invention may be useful in the treatment or prevention of diseases or conditions such as for example infections caused by dermatophytes, systemic fungal infections or onychomycosis.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the treatment or prevention, in particular treatment, of fungal infections, in particular fungal infections caused by one or more of the fungi mentioned hereinbefore.

The compounds of the present invention can be administered to mammals, preferably humans, for the treatment or prevention, in particular treatment, of fungal infections, in particular fungal infections caused by one or more of the fungi mentioned hereinbefore.

In view of the utility of the compound of Formula (I), there is provided a method of treating warm-blooded animals, including humans, suffering from or a method of preventing warm-blooded animals, including humans, to suffer from fungal infections, in particular fungal infections caused by one or more of the fungi mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

While it is possible for the active ingredient to be administered alone, it is preferable to present it as a pharmaceutical composition.

The present invention also provides compositions for treating or preventing fungal infections comprising a therapeutically effective amount of a compound of Formula (I) and a pharmaceutically acceptable carrier or diluent.

The carrier or diluent must be "acceptable" in the sense of being compatible with the other ingredients of the composition and not deleterious to the recipients thereof.

The compounds of the present invention, that are suitable to treat or prevent fungal infections, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

In view of their useful pharmacological properties, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

For parenteral compositions, also other ingredients, to aid solubility for example, e.g. cyclodextrins, may be included. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of Formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of Formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of Formula (I), or amorphous, microcrystalline or crystalline water-soluble polymer, or both, are dispersed more or less evenly in another phase comprising water-soluble polymer, or compound of Formula (I), or a solid solution comprising compound of Formula (I) and water-soluble polymer. Said domains are regions within the solid dispersion distinctively marked by some physical feature, small in size, and evenly and randomly distributed throughout the solid dispersion.

It may further be convenient to formulate the present antifungal compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

Since the compounds according to the invention are potent orally administrable compounds, pharmaceutical compositions comprising said compounds for administration orally are especially advantageous.

The following examples illustrate the present invention.

EXPERIMENTAL PART

Hereinafter, the term "DCM" means dichloromethane; "MeOH" means methanol; "LCMS" means Liquid Chromatography/Mass spectrometry; "HPLC" means high-performance liquid chromatography; "r.t." means room temperature; "m.p." means melting point; "min" means minute(s); "h" means hour(s); "I.D." means internal diameter; "EtOAc" means ethyl acetate; "Et$_3$N" means triethylamine; "EtOH" means ethanol; "eq." means equivalent; "r.m." means reaction mixture(s); "q.s." quantum sufficit; "SFC" means supercritical fluid chromatography; "THF" means tetrahydrofuran; "HOAc" means acetic acid; "DEA" means diethylamine, "HOBt" means 1-hydroxy-1H-benzotriazole; "Me$_2$S" means dimethyl sulfide; "Pd(PPh$_3$)$_2$Cl$_2$" means dichlorobis(triphenylphosphine)palladium; and "EDCI" means N'-(ethylcarbonimidoyl)-N,N-dimethyl-1,3-propanediamine monohydrochloride.

A. Preparation of the Intermediates

Example A1 a-1) Preparation of Intermediate 1

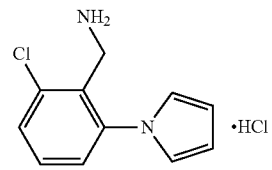 [SMILES: NCc1c(Cl)cccc1-n1cccc1 ; Cl]

2-Chloro-6-(1H-pyrrol-1-yl)-benzonitrile (50 g, 0.2467 mol) was dissolved in THF (500 ml). A 10.0 M solution of BH₃ in Me₂S (27.1 ml, 0.2714 mol) was added dropwise to this solution at r.t. The r.m. was then stirred and refluxed for 12 h. Subsequently, the mixture was cooled to r.t. and a 6 N HCl solution (47 ml) was added dropwise. The r.m. was heated under reflux temperature for 30 min. The clear solution is cooled to 0° C. and NaOH (55.5 g) was added. The mixture was extracted with EtOAc and saturated brine. The organic layer was dried (MgSO₄), filtered and the solvent was evaporated, yielding 46.5 g of the product as a free base. Subsequently, the product was acidified by HCl/dioxane (q.s.) to obtain 55 g of intermediate 1 (97% yield; .HCl).

a-2) Alternative Procedure for the Preparation of Intermediate 1

A mixture of 2-Chloro-6-(1H-pyrrol-1-yl)-benzonitrile (0.08 mol) in MeOH/NH₃ (250 ml) was hydrogenated at 14° C. with Raney Nickel (2 g) as a catalyst, in the presence of a 4% thiophene solution in MeOH (2 ml). After uptake of H₂ (2 eq.), the catalyst was filtered off and the filtrate was evaporated. Subsequently, a 6 N 2-propanol/HCl solution (14 ml) was added. Then, the solvent was evaporated, yielding a mixture of 2-(1H-pyrrol-1-yl)-benzenemethanamine and intermediate 1 as a HCl-salt form (.HCl). This mixture was used as such without further purification in the next reaction step.

Example A2

Preparation of Intermediate 2

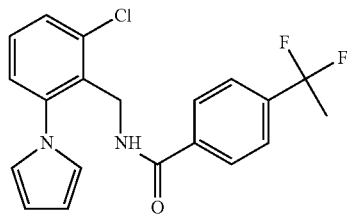 [SMILES: CC(F)(F)c1ccc(C(=O)NCc2c(Cl)cccc2-n2cccc2)cc1]

4-(1,1-difluoroethyl)-benzoic acid (5.05 g, 27.1 mmol) was dissolved in DCM (100 ml). Et₃N (10 ml, 60.9 mmol), HOBt (3.6 g, 27.1 mmol), EDCI (5.18 g, 27.1 mmol) and intermediate 1 (6.0 g, 24.7 mmol) were added to this solution and the r.m. was stirred overnight. Subsequently, water (q.s.) was added and the mixture was extracted with DCM. The separated organic layer was dried (Na₂SO₄), filtered, and the solvent was evaporated. The residue was purified by column chromatography (petrol ether/EtOAc gradient elution from 15/1 to 10/1). The product fractions were collected and the solvent was evaporated in vacuo to yield 8.2 g of intermediate 2 (88.6% yield).

Example A3 a) Preparation of Intermediate 3

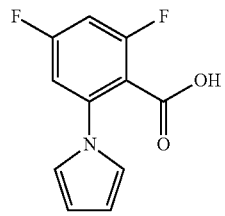 [SMILES: O=C(O)c1c(F)cc(F)cc1-n1cccc1]

A mixture of 2-amino-4,6-difluorobenzoic acid (60 g, 346 mmol), tetrahydro-2,5-dimethoxyfuran (45.7 g, 346 mmol) and pyridine hydrochloride (1:1) (40 g, 346 mmol) in dioxane (500 ml) was heated to reflux overnight. Subsequently, the solvent was evaporated and the residue was dissolved in EtOAc (100 ml). This solution was washed with brine and water. The organic layer was separated, dried (MgSO₄), filtered and the solvent was evaporated. Yield: 70 g of crude intermediate 3, which was used as such in the next reaction step.

b) Preparation of Intermediate 4

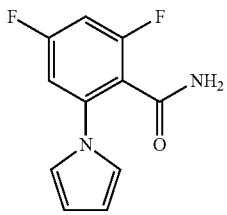 [SMILES: NC(=O)c1c(F)cc(F)cc1-n1cccc1]

NH₃.H₂O (100 ml) was added to a solution of intermediate 3, HOBt (47 g, 346 mmol) and EDCI (70 g, 346 mmol) in DMF (300 ml). The r.m. was stirred overnight. Subsequently the solvent was evaporated, and the residue was dissolved in EtOAc. This organic solution was first washed with brine and water, then dried (MgSO₄) and filtered, and finally the solvent was evaporated. Yield: 55 g of crude intermediate 4, which was used as such in the next reaction step.

c) Preparation of Intermediate 5

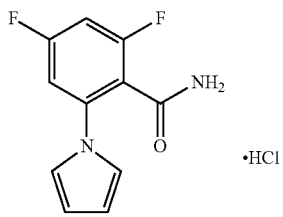 [SMILES: NC(=O)c1c(F)cc(F)cc1-n1cccc1 ; Cl]

BH₃.Me₂S (10 M solution; 40.5 ml, 405 mmol) was added to a mixture of intermediate 4 (45 g, 202.5 mmol) in THF (500 ml). The r.m. was refluxed overnight under N₂ atmosphere. Subsequently the mixture was cooled on an ice-water bath and a 6 N HCl solution (10 ml) was added. The mixture was refluxed again for 30 minutes. The mixture was cooled on an ice-water bath and solid NaOH was added until pH>9. The mixture was extracted with DCM (2 times 300 ml). The organic layers were separated, combined, dried (MgSO$_4$), filtered and the solvent was evaporated. The brown residue was converted to its HCl salt form (1:1) with HCl/2-propanol, yielding 35 g of intermediate 5 (71% yield).

d) Preparation of Intermediate 6

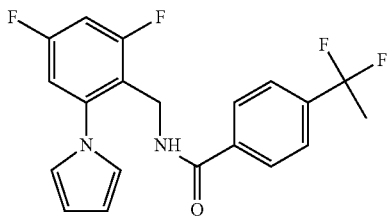 [SMILES: CC(F)(F)c1ccc(C(=O)NCc2c(F)cc(F)cc2-n2cccc2)cc1]

4-(1,1-difluoroethyl)benzoic acid (1.17 g, 6.13 mmol) was dissolved in DCM (50 ml). Et$_3$N (7.3 ml), HOBt (0.828 g, 6.13 mmol), EDCI (1.17 g, 6.13 mmol) and intermediate 5 (1.5 g, 6.13 mmol) were added to the solution, and the r.m. was stirred overnight at r.t. Subsequently, the solvent was evaporated and water was added to the residue. The aqueous mixture was extracted with DCM. The organic layer was separated, dried (Na$_2$SO$_4$), filtered and the solvent was evaporated. Yield: 1.4 g of intermediate 6 (60% yield).

Example A4 a) Preparation of Intermediate 7

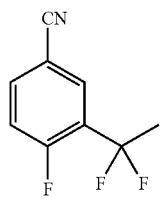

3-acetyl-4-fluorobenzonitrile (11.0 g, 67.4 mmol) was dissolved in (diethylamino)sulfur trifluoride (25 ml) under N$_2$ flow. The solution was heated to 50° C. for 16 h. and was then poured into a NaHCO$_3$ solution (q.s.). This mixture was extracted with EtOAc. The organic layer was separated, dried (Na$_2$SO$_4$), filtered and the solvent was evaporated under reduced pressure. The residue was purified by column chromatography over silica gel (eluent: petroleum ether/EtOAc from 30/1 to 20/1). The desired fractions were collected and the solvent was evaporated in vacuo. Yield: 10.5 g of intermediate 7 (84% yield).

b) Preparation of Intermediate 8

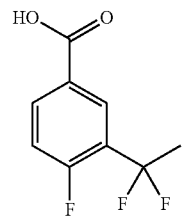

A mixture of intermediate 7 (8.2 g, 5.7 mmol) in a 20% NaOH solution (50.0 ml) and EtOH (20.0 ml) was refluxed and stirred overnight. Subsequently, the mixture was concentrated in vacuo. HCl was added till pH 2 and a precipitate was formed. The precipitate was filtered off and dried in vacuo. The solid was used as such in the next reaction step. Yield: 9.2 g of intermediate 8.

c) Preparation of Intermediate 9

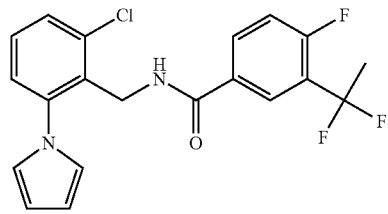 [SMILES: CC(F)(F)c1cc(C(=O)NCc2c(Cl)cccc2-n2cccc2)ccc1F]

A mixture of intermediate 1 (1.0 g, 4.2 mmol), intermediate 8 (1.0 g, 5.0 mmol), Et$_3$N (5.0 ml, 36 mmol), HOBt (0.62 g) and EDCI (0.96 g) in DCM (40 ml) was stirred overnight at r.t. The resulting mixture was washed with water (3 times 100 ml), dried (MgSO$_4$), filtered and the solvent was evaporated under reduced pressure. The residue was purified by column chromatography over silica gel (eluent: petroleum ether/EtOAc from 20/1 to 10/1). The desired fractions were collected and the solvent was evaporated in vacuo. Yield: 0.9 g of intermediate 9 (59.6% yield).

Example A5 a) Preparation of Intermediate 10

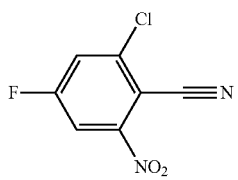

Tert-butyl nitrite (25 g, 242 mmol) was added to a suspension of CuCN (21.5 g, 242 mmol) in CH$_3$CN (500 ml). The mixture was heated to 70° C. and was stirred for 15 min. Subsequently, a mixture of 2-chloro-4-fluoro-6-nitrobenzenamine (23 g, 121 mmol) and CH$_3$CN (q.s.) was added, and the resulting brown solution was heated overnight at 70° C. The solvent was removed in vacuo. Water (q.s.) was added to the residue and the aqueous mixture was extracted with EtOAc. The separated organic layer was dried (MgSO$_4$), filtered, and the solvent was evaporated. The residue was purified by column chromatography over silica gel (eluent: EtOAc/petroleum ether 1/4). The desired fractions were collected and the solvent was evaporated. Yield: 10 g of intermediate 10 (41% yield; yellow solid).

b) Preparation of Intermediate 11

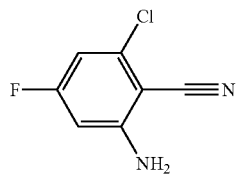

Fe (11.6 g, 200 mmol) was added portionwise to a solution of intermediate 10 (10 g, 50 mmol) in HOAc (250 ml). The r.m. was heated to 70° C. for 1 h, and was then cooled to r.t. The solid was filtered off and the solvent was evaporated. The residue was dissolved in EtOAc, washed with aqueous NaHCO$_3$ and water. The organic layer was dried (MgSO$_4$), filtered and the solvent was evaporated. Yield: 6.2 g of intermediate 11 which was used as such in the next reaction step.

c) Preparation of Intermediate 12

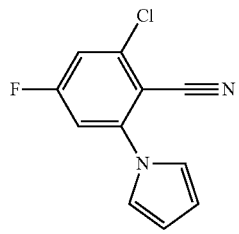 [SMILES: N#Cc1c(Cl)cc(F)cc1-n1cccc1]

A solution of intermediate 11 (6 g, 35 mmol) and tetrahydro-2,5-dimethoxy-furan (4.66 g, 35 mmol) in HOAc (50 ml) was heated at reflux temperature for 6 h. Then, the solvent was evaporated and the residue was purified by column chromatography over silica gel (eluent: DCM). The desired fractions were collected and the solvent was evaporated. Yield: 4.6 g of intermediate 12 (90% yield).

d) Preparation of Intermediate 13

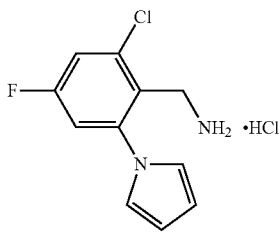 [SMILES: NCc1c(Cl)cc(F)cc1-n1cccc1 ; Cl]

A 10 M solution of BH$_3$.Me$_2$S (2 ml; 20 mmol) was added to a mixture of intermediate 12 (4.4 g, 20 mmol) in THF (50 ml). The r.m. was refluxed overnight under N$_2$ atmosphere. Subsequently, the mixture was cooled on an ice-water bath and a 6 N HCl solution (10 ml) was carefully added to the mixture. The solution was then refluxed again for 30 min, and was then cooled again on an ice-water bath. Solid NaOH was added till pH>9. The mixture was extracted with DCM (2 times 300 ml). The separated organic layer was dried (MgSO$_4$), filtered and the solvent was evaporated. The brown residue was converted to the HCl salt (1:1) with HCl/2-propanol. Yield: 5 g of intermediate 13 (96% yield).

Example A6 a) Preparation of Intermediate 14

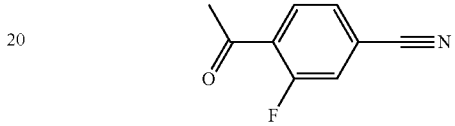

Reaction under N$_2$ atmosphere: A mixture of 4-bromo-3-fluorobenzonitrile (6.0 g, 30.00 mmol) and (1-ethoxyethenyl)tributyltin (11.2 ml, 33.00 mmol) in toluene (100 ml) was stirred at r.t. Pd(PPh$_3$)$_2$Cl$_2$ (0.72 g, 1.03 mmol) was added to the mixture, and the r.m. was heated at refluxed temperature and stirred overnight. The mixture was cooled and a 2 N KF solution (50 ml) was added to the mixture while stirring. After 30 min, a 6 N HCl solution was added (100 ml) to the mixture, and the mixture was heated to 70° C. and stirred for 2 h. The insoluble substance was filtered off, and the filtrate was extracted with EtOAc (3 times 80 ml). The combined organic layers were washed with brine, dried (MgSO$_4$), filtered and the solvent was evaporated in vacuo. Yield: 4.3 g of intermediate 14 (88% yield).

Intermediate 14 can be reacted further analogous to the reaction protocol described in Example A4, to obtain compound 29.

Example A7 a) Preparation of Intermediate 15

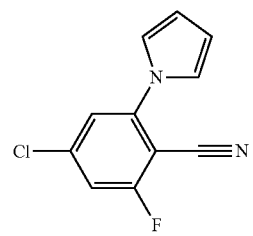 [SMILES: N#Cc1c(F)cc(Cl)cc1-n1cccc1]

A mixture of 4-chloro-2,6-difluorobenzonitrile (1.66 g, 9.56 mmol), pyrrole (0.67 g, 10 mmol) and Cs$_2$CO$_3$ (3.7 g, 12 mmol) in DMF (20 ml) was stirred overnight. Then, the solid was filtered off and the solvent was removed by reduced pressure. The residue was purified by column chromatography over silica gel (eluent: EtOAc/petroleum ether 10/1). The desired fractions were collected and the solvent was evaporated. Yield: 1.1 g of intermediate 15 (15% yield; white solid).

Intermediate 15 can be reacted further analogous to the reaction protocol described in Example A1, to obtain compound 32.

B. Preparation of the Compounds

Example B1 a) Preparation of Compound 1

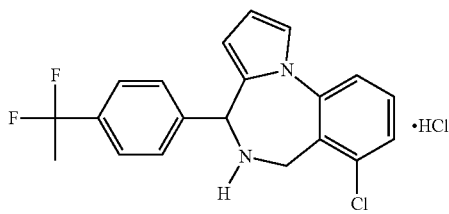

A mixture of intermediate 1 (9.5 g, 39.2 mmol) and 4-(1,1-difluoroethyl)-benzaldehyde (8.0 g, 47.0 mmol) in EtOH (15 ml) was stirred and refluxed for 4 h. Subsequently, the mixture was cooled and crystallized overnight. The precipitate was filtered off, washed with isopropylether, and dried in vacuo. Yield: 8.0 g of compound 1 (52.2% yield).

b) Preparation of Compound 2 and Compound 3

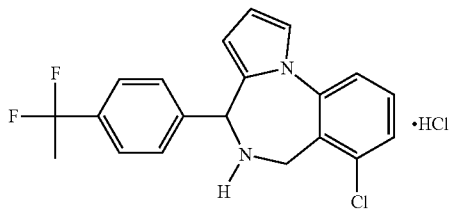 [SMILES: CC(F)(F)c1ccc(C2NCc3c(Cl)cccc3-n3cccc32)cc1 ; Cl]

Compound 2: S enantiomer; Compound 3: R enantiomer

Compound 1 was separated into its enantiomers by chiral SFC (Column AD 300 mm*50 mm, 20 μM; Mobile phase: CO$_2$/MeOH (0.2% DEA) 60/40; Flow: 200 ml/min) Two different fractions were collected, and both fractions were converted to the HCl salt form with HCl/EtOH 1/1.

Yield: 3.2 g of compound 2 (20.8% yield; S configuration).

Yield: 3.0 g of compound 3 (19.6% yield; R configuration).

Example B2 a) Preparation of Compound 4

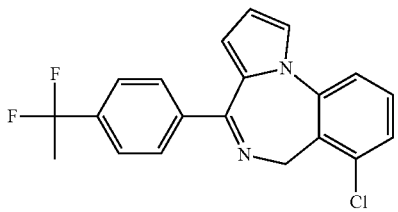 [SMILES: CC(F)(F)c1ccc(C2=NCc3c(Cl)cccc3-n3cccc32)cc1]

A mixture of compound 1 (0.334 g, 0.0009 mol) and MnO$_2$ (2.6 g, 0.0299 mol) in DCM (15 ml) was stirred for 96 h at r.t. Subsequently, the precipitate was filtered off over diatomaceous earth and the filtrate was evaporated. The residue was purified by preparative HPLC, yielding 0.19 g of compound 4 (59%).

b) Alternative Preparation of Compound 4

Intermediate 2 (4.0 g, 10.67 mmol) was dissolved in POCl$_3$ (12 ml). The mixture was stirred and refluxed overnight. Subsequently, the mixture was cooled and poured into water. The aqueous mixture was neutralized with NaOH to pH 7, and was then extracted with DCM. The separated organic layer was dried (Na$_2$SO$_4$), filtered and the solvent was evaporated. The residue was crystallized from EtOH, yielding compound 4 (56.3% yield).

Example B3 a) Preparation of Compound 18

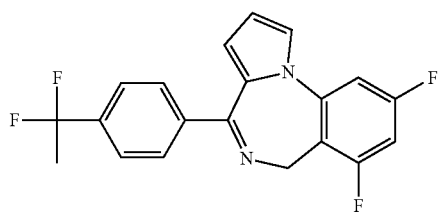 [SMILES: CC(F)(F)c1ccc(C2=NCc3c(F)cc(F)cc3-n3cccc32)cc1]

Intermediate 6 (1.4 g, 3.71 mmol) was dissolved in POCl$_3$ (10 ml). The mixture was stirred and refluxed overnight. Subsequently, the mixture was cooled and poured into water. The aqueous mixture was neutralized with NaOH till pH 7, and was then extracted with DCM. The organic layer was separated, dried (MgSO$_4$), filtered and concentrated. The residue was purified by flash column chromatography over silica gel (eluent: petroleum ether/EtOAc 4/1). The product fractions were collected and the solvent was evaporated to yield 150 mg of compound 118 (21.6% yield).

Example B4 a) Preparation of Compound 21

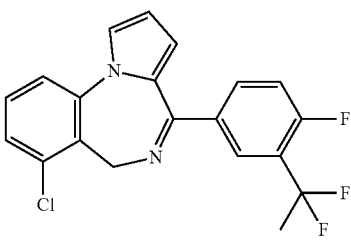 [SMILES: CC(F)(F)c1cc(C2=NCc3c(Cl)cccc3-n3cccc32)ccc1F]

Intermediate 9 (0.80 g, 2.0 mmol) was dissolved in POCl$_3$ (3 ml). The mixture was stirred overnight at 100° C. Subsequently, the r.m. was poured out into ice water. NaOH was added to pH 8-9. The mixture was then extracted with DCM. The organic layers were separated, dried (Na$_2$SO$_4$), filtered and the solvent was evaporated in vacuo. The residue was purified by column chromatography over silica gel (eluent:

petroleum ether/EtOAc from 10/1 to 5/1). The desired fractions were collected and the solvent was evaporated in vacuo. Yield: 0.510 g of compound 21 (yield 68%).

Example B5 a) Preparation of Compound 24

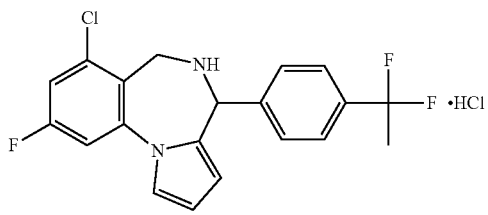 [SMILES: CC(F)(F)c1ccc(C2NCc3c(Cl)cc(F)cc3-n3cccc32)cc1 ; Cl]

A solution of intermediate 13 (0.52 g, 2 mmol) and 4-(1,1-difluoroethyl)benzaldehyde (0.374 g, 2 mmol) in EtOH (5 ml) was heated to reflux for 4 h. Subsequently, the mixture was cooled to room temperature and the solid was collected and dried. Yield: 0.6 g of compound 24 (80% yield; .HCl).

By using analogous reaction protocols as described in the foregoing examples, the following compounds have been prepared. 'Co. No.' means compound number. 'Pr.' refers to the Example number according to which protocol the compound was synthesized. In case no salt form is indicated, the compound was obtained as a free base.

Compounds wherein $R^3$ and $R^4$ are hydrogen, and for which no specific stereochemistry is indicated in Table 1, were obtained as mixtures of enantiomers. In case a final compound obtained by using an analogous protocol as described in B1 or B5, was not fully converted to the HCl salt form, the compound was converted to the HCl salt form by using procedures known to those skilled in the art. In a typical procedure, the compound was dissolved in a solvent such as, for example, 2-propanol, and subsequently a HCl solution in a solvent such as, for example, 2-propanol was added drop wise. Stirring for a certain period of time, typically about 10 minutes, could enhance the rate of the reactions.

TABLE 1

(I)

| Co. No. | Pr. | $R^1$ | $R^2$ | $R^3$ | $R^4$ | $R^5$ | $R^6$ | Salt Form/ Optical rotation (OR)/ Stereo- chemistry |
|---|---|---|---|---|---|---|---|---|
| 1 | B1.a | 7-Cl | H | H | H | $CF_2CH_3$ | H | •HCl |
| 2 | B1.b | 7-Cl | H | H | H | $CF_2CH_3$ | H | •HCl OR: −172.64° (589 nm; 20° C.; 0.3684 w/v %; MeOH) S-configuration |
| 3 | B1.b | 7-Cl | H | H | H | $CF_2CH_3$ | H | •HCl OR: +168.90° (589 nm; 20° C.; 0.3434 w/v %; MeOH) R-configuration |
| 4 | B2.a/ B2.b | 7-Cl | H | bond | H | $CF_2CH_3$ | H | |
| 5 | B1.a | 8-Cl | 10-Cl | H | H | $CF_2CH_3$ | H | •HCl |
| 6 | B2.a | 8-Cl | 10-Cl | bond | | $CF_2CH_3$ | H | |
| 7 | B1.a | 7-Cl | 8-Cl | H | H | $CF_2CH_3$ | H | •HCl |
| 8 | B2.a | 7-Cl | 10-Cl | bond | | $CF_2CH_3$ | H | |
| 9 | B2.a | 7-Cl | 9-Cl | bond | | $CF_2CH_3$ | H | |
| 10 | B2.a | 7-Cl | 8-Cl | bond | | $CF_2CH_3$ | H | |
| 11 | B5 | 7-Cl | 10-Cl | H | H | $CF_2CH_3$ | H | •HCl |
| 12 | B1.a | 7-Cl | H | H | H | H | $CF_2CH_3$ | •HCl |
| 13 | B5 | 7-Cl | 9-Cl | H | H | $CF_2CH_3$ | H | •HCl |
| 14 | B2.a | 7-Cl | H | bond | | H | $CF_2CH_3$ | |
| 15 | B2.a | 7-F | H | bond | | $CF_2CH_3$ | H | |
| 16 | B3 | 9-Cl | 7-$CH_3$ | bond | | $CF_2CH_3$ | H | |
| 17 | B3 | 9-Cl | H | bond | | $CF_2CH_3$ | H | |
| 18 | B3 | 7-F | 9-F | bond | | $CF_2CH_3$ | H | |
| 19 | B3 | 10-Cl | H | bond | | $CF_2CH_3$ | H | |
| 20 | B4 | 7-F | H | bond | | F | $CF_2CH_3$ | |
| 21 | B4 | 7-Cl | H | bond | | F | $CF_2CH_3$ | |
| 22 | B4 | 9-Cl | 10-Cl | bond | | $CF_2CH_3$ | H | |
| 23 | B4 | 7-F | 9-F | bond | | F | $CF_2CH_3$ | |
| 24 | B5 | 7-Cl | 9-F | H | H | $CF_2CH_3$ | H | •HCl |
| 25 | B4 | 7-Cl | 9-Cl | bond | | F | $CF_2CH_3$ | |
| 26 | B4 | 7-Cl | 9-F | bond | | F | $CF_2CH_3$ | |
| 27 | B2.a | 7-Cl | 9-F | bond | | $CF_2CH_3$ | H | |
| 28 | B4 | 10-Cl | 7-$CH_3$ | bond | | $CF_2CH_3$ | H | |
| 29 | B4 | 7-Cl | H | bond | | $CF_2CH_3$ | F | |
| 30 | B4 | 7-F | H | bond | | $CF_2CH_3$ | F | |
| 31 | B4 | 7-Cl | 9-F | bond | | $CF_2CH_3$ | F | |
| 32 | B4 | 7-F | 9-Cl | bond | | $CF_2CH_3$ | H | |
| 33 | B4 | 7-F | 9-F | bond | | $CF_2CH_3$ | F | |
| 34 | B4 | 9-Cl | H | bond | | F | $CF_2CH_3$ | |
| 35 | B4 | H | 10-Cl | bond | | F | $CF_2CH_3$ | |

C. Analytical Results

LCMS

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 μm column with a flow rate of 0.8 ml/min. 2 mobile phases (mobile phase A: water with 0.1% TFA; mobile phase B: $CH_3CN$ with 0.05% TFA) were used. First, 90% A and 10% B was hold for 0.8 min. Then a gradient was applied to 20% A and 80% B in 3.7 min and hold for 3 min. Typical injection volumes of 2 μl were used. Oven temperature was 50° C. (MS polarity: positive)

Melting Points

For a number of compounds, melting points (m.p.) were determined with a WRS-2A melting point apparatus purchased from Shanghai Precision and Scientific Instrument Co. Ltd. Melting points were measured with a linear heating up rate of 0.2-5.0° C./min The reported values are melt ranges. The maximum temperature was 300° C.

The results of the analytical measurements are shown in table 2.

TABLE 2

Retention time ($R_t$) in min., [M + H]$^+$ peak (protonated molecule), and m.p. (melting point in ° C.).

| Co. No. | $R_t$ | [M + H]$^+$ | m.p. (° C.) |
|---|---|---|---|
| 1 | 3.57 | 359 | n.d. |
| 2 | 3.38 | 359 | 206.7-207.6 |
| 3 | 3.33 | 359 | 206.3-206.8 |
| 4 | 3.59 | 357 | 215.2-217.6 |
| 5 | 4.00 | 393 | n.d. |
| 6 | 4.03 | 391 | 132.1-134.2 |
| 7 | 3.95 | 393 | 253.5-254.2 |
| 8 | 3.99 | 391 | 162.3-163.5 |
| 9 | 4.03 | 391 | n.d. |
| 10 | 4.03 | 391 | n.d. |
| 11 | 4.04 | 393 | 188.5-191.1 |
| 12 | n.d. | n.d. | n.d. |
| 13 | 4.11 | 393 | 233.9-235.0 |
| 14 | 3.51 | 357 | 106.9-109.7 |
| 15 | 3.27 | 341 | n.d. |
| 16 | 3.97 | 371 | 89.6-91.2 |
| 17 | 3.53 | 357 | 115.3 dec |
| 18 | 3.31 | 359 | n.d. |
| 19 | 3.52 | 357 | 247.5 dec |
| 20 | 3.46 | 359 | n.d. |
| 21 | 3.56 | 375 | n.d. |
| 22 | 3.84 | 391 | 140.9-142.1 |
| 23 | 3.48 | 377 | 143.2-144.3 |
| 24 | 3.53 | 377 | 240.0-240.7 |
| 25 | 3.77 | 409 | 124.2-125.4 |
| 26 | 3.53 | 393 | 84.9-85.9 |
| 27 | 3.84 | 375 | n.d. |
| 28 | 3.71 | 371 | 139.3-141.2 |
| 29 | 3.44 | 375 | 186.3-186.6 |
| 30 | 3.25 | 359 | 170.8-171.5 |
| 31 | 3.44 | 393 | 162.5-164.8 |
| 32 | 3.31 | 375 | 145.3-147.4 |
| 33 | 3.23 | 377 | 158.2-161.3 |
| 34 | 3.95 | 375 | n.d. |
| 35 | 3.97 | 375 | n.d. |

("n.d." means not determined; "dec" means decomposed).

$^1$H NMR

For a number of compounds, $^1$H NMR spectra were recorded on a Bruker DPX-300, or on a Bruker DPX-400 spectrometer with standard pulse sequences, operating at 300 MHz and 400 MHz respectively, using CHLOROFORM-d (deuterated chloroform, $CDCl_3$) or DMSO-$d_6$ (deuterated DMSO, dimethyl-d6 sulfoxide) as solvents. Chemical shifts (δ) are reported in parts per million (ppm) relative to tetramethylsilane (TMS), which was used as internal standard.

Co. No. 1: (300 MHz, DMSO-$d_6$) δ ppm 2.01 (t, J=18.9 Hz, 3H) 3.87 (d, J=14.3 Hz, 1H) 4.57 (d, J=13.9 Hz, 1H) 5.35 (br. s., 1H) 5.84 (br. s., 1H) 6.30 (t, J=3.2 Hz, 1H) 7.43 (br. s., 1H) 7.57-7.77 (m, 5H) 7.90 (d, J=8.1 Hz, 2H) 10.45 (br. s., 2H).

Co. No. 2: (300 MHz, DMSO-$d_6$) δ ppm 2.01 (t, J=18.93 Hz, 3H) 3.88 (d, J=14.32 Hz, 1H) 4.58 (d, J=13.94 Hz, 1H) 5.35 (br. s., 1H) 5.84 (br. s., 1H) 6.31 (t, J=3.20 Hz, 1H) 7.44 (br. s., 1H) 7.57-7.78 (m, 5H) 7.90 (d, J=8.10 Hz, 2H) 10.45 (br. s., 2H).

Co. No. 3: (300 MHz, DMSO-$d_6$) δ ppm 2.01 (t, J=18.93 Hz, 3H) 3.88 (d, J=14.13 Hz, 1H) 4.58 (d, J=13.94 Hz, 1H) 5.35 (br. s., 1H) 5.84 (d, J=2.64 Hz, 1H) 6.31 (t, J=3.20 Hz, 1H) 7.43 (dd, J=2.64, 1.51 Hz, 1H) 7.56-7.79 (m, 5H) 7.90 (d, J=7.91 Hz, 2H) 10.40 (br. s., 2H).

Co. No. 4: (300 MHz, $CDCl_3$) δ ppm 1.84 (t, J=18.08 Hz, 3H) 4.13 (br. s., 1H) 5.44 (br. s., 1H) 6.25-6.54 (m, 2H) 7.19-7.24 (m, 2H) 7.25-7.35 (m, 2H) 7.42 (m, J=8.29 Hz, 2H) 7.69 (m, J=8.10 Hz, 2H).

Co. No. 5: (400 MHz, DMSO-$d_6$) δ ppm 2.01 (t, J=18.97 Hz, 3H) 3.62 (d, J=13.32 Hz, 1H) 4.39 (d, J=13.32 Hz, 1H) 5.41 (br. s., 1H) 5.88 (d, J=2.83 Hz, 1H) 6.30 (t, J=3.23 Hz, 1H) 7.40 (dd, J=3.03, 1.41 Hz, 1H) 7.70 (m, J=8.07 Hz, 2H) 7.80 (d, J=2.42 Hz, 1H) 7.91 (m, J=8.07 Hz, 2H) 8.07 (d, J=2.42 Hz, 1H) 10.26 (br. s., 1H) 10.66 (br. s., 1H).

Co. No. 6: (400 MHz, $CDCl_3$) δ ppm 1.93 (t, J=18.1 Hz, 3H) 4.28 (d, J=11.0 Hz, 1H) 4.87 (d, J=11.0 Hz, 1H) 6.47 (br. s., 1H) 6.57 (br. s., 1H) 7.41-7.66 (m, 5H) 7.88 (d, J=7.8 Hz, 2H).

Co. No. 8: (400 MHz, $CDCl_3$) δ ppm 1.92 (t, J=18.2 Hz, 3H) 4.08 (d, J=11.3 Hz, 1H) 5.46 (d, J=11.3 Hz, 1H) 6.38-6.46 (m, 1H) 6.51 (d, J=2.5 Hz, 1H) 7.34 (d, J=8.5 Hz, 1H) 7.39 (d, J=8.5 Hz, 1H) 7.46-7.58 (m, 3H) 7.87 (d, J=8.3 Hz, 2H).

Co. No. 9: (400 MHz, $CDCl_3$) δ ppm 1.92 (t, J=18.2 Hz, 3H) 4.16 (br. s., 1H) 5.49 (br. s., 1H) 6.38-6.57 (m, 2H) 7.30 (d, J=2.0 Hz, 1H) 7.34 (br. s., 1H) 7.41 (d, J=1.8 Hz, 1H) 7.51 (m, J=8.3 Hz, 2H) 7.76 (m, J=8.3 Hz, 2H).

Co. No. 10: (400 MHz, $CDCl_3$) δ ppm 1.95 (t, J=18.3 Hz, 3H) 4.46 (br. s., 1H) 5.82 (br. s., 1H) 6.80 (dd, J=4.3, 2.8 Hz, 1H) 7.04 (dd, J=4.3, 1.5 Hz, 1H) 7.29 (d, J=8.8 Hz, 1H) 7.66 (d, J=8.5 Hz, 1H) 7.69 (m, J=8.3 Hz, 2H) 7.79-7.85 (m, 1H) 7.90 (d, J=8.3 Hz, 2H).

Co. No. 11: (300 MHz, DMSO-$d_6$) δ ppm 2.01 (t, J=18.8 Hz, 3H) 3.59 (d, J=14.3 Hz, 1H) 4.57 (d, J=14.3 Hz, 1H) 5.44 (br. s., 1H) 5.91 (br. s., 1H) 6.32 (t, J=3.2 Hz, 1H) 7.42 (br. s., 1H) 7.65-7.79 (m, 3H) 7.83 (d, J=7.9 Hz, 2H) 7.89 (d, J=8.7 Hz, 1H).

Co. No. 13: (300 MHz, DMSO-$d_6$) δ ppm 2.01 (t, J=19.0 Hz, 3H) 3.83 (d, J=14.3 Hz, 1H) 4.53 (d, J=13.9 Hz, 1H) 5.42 (br. s., 1H) 5.83 (br. s., 1H) 6.30 (t, J=3.0 Hz, 1H) 7.49 (br. s., 1H) 7.70 (d, J=7.9 Hz, 2H) 7.77-7.94 (m, 4H) 10.42 (br. s., 2H).

Co. No. 14: (300 MHz, $CDCl_3$) δ ppm 1.90 (t, J=18.1 Hz, 3H) 4.17 (br. s., 1H) 5.50 (br. s., 1H) 6.43-6.55 (m, 2H) 7.22-7.30 (m, 2H) 7.30-7.45 (m, 3H) 7.56 (d, J=7.5 Hz, 1H) 7.76 (d, J=7.9 Hz, 1H) 7.84 (s, 1H).

Co. No. 15: (400 MHz, $CDCl_3$) δ ppm 1.92 (t, J=18.2 Hz, 3H) 4.74 (s, 2H) 6.43-6.51 (m, 1H) 6.53 (dd, J=3.8, 1.5 Hz, 1H) 7.09 (t, J=8.3 Hz, 1H) 7.18 (d, J=8.3 Hz, 1H) 7.35 (td, J=8.1, 5.9 Hz, 1H) 7.39-7.43 (m, 1H) 7.52 (m, J=8.3 Hz, 2H) 7.78 (m, J=8.3 Hz, 2H).

Co. No. 16: (300 MHz, $CDCl_3$) δ ppm 1.93 (t, J=18.18 Hz, 3H) 2.60 (s, 3H) 4.13 (br. s., 1H) 5.17 (br. s., 1H)

6.42-6.53 (m, 2H) 7.20 (d, J=1.88 Hz, 1H) 7.24 (d, J=1.88 Hz, 1H) 7.33-7.40 (m, 1H) 7.52 (m, J=8.29 Hz, 2H) 7.75 (m, J=8.29 Hz, 2H).

Co. No. 18: (400 MHz, CDCl$_3$) δ ppm 1.92 (t, J=18.1 Hz, 3H) 4.69 (br. s., 2H) 6.45-6.49 (m, 1H) 6.49-6.53 (m, 1H) 6.84 (td, J=9.0, 2.4 Hz, 1H) 6.95 (dt, J=9.0, 1.9 Hz, 1H) 7.33 (dd, J=2.8, 1.5 Hz, 1H) 7.51 (m, J=8.3 Hz, 2H) 7.75 (m, J=8.3 Hz, 2H).

Co. No. 20: (400 MHz, CDCl$_3$) δ ppm 2.00 (t, J=18.6 Hz, 3H) 4.77 (br. s., 2H) 6.53 (br. s., 1H) 6.59 (br. s., 1H) 7.06-7.26 (m, 3H) 7.33-7.44 (m, 1H) 7.47 (br. s., 1H) 7.90 (br. s., 1H) 7.95 (d, J=6.5 Hz, 1H).

Co. No. 21: (300 MHz, CDCl$_3$) δ ppm 2.01 (t, J=18.6 Hz, 3H) 4.24 (br. s., 1H) 5.62 (br. s., 1H) 6.50-6.79 (m, 2H) 7.16-7.33 (m, 2H) 7.38 (t, J=7.9 Hz, 1H) 7.43-7.62 (m, 2H) 7.85-8.15 (m, 2H).

Co. No. 22: (400 MHz, CDCl$_3$) δ ppm 1.92 (t, J=18.1 Hz, 3H) 4.24 (d, J=11.3 Hz, 1H) 4.82 (d, J=11.3 Hz, 1H) 6.39-6.46 (m, 1H) 6.49 (dd, J=3.9, 1.4 Hz, 1H) 7.37 (d, J=8.0 Hz, 1H) 7.44 (d, J=8.3 Hz, 1H) 7.51 (m, J=8.3 Hz, 2H) 7.55 (dd, J=2.8, 1.5 Hz, 1H) 7.83 (m, J=8.5 Hz, 2H).

Co. No. 23: (400 MHz, CDCl$_3$) δ ppm 2.00 (t, J=18.6 Hz, 3H) 5.03 (br. s., 2H) 6.45-6.52 (m, 2H) 6.85 (td, J=9.0, 2.4 Hz, 1H) 6.95 (d, J=9.3 Hz, 1H) 7.07-7.18 (m, 1H) 7.33 (t, J=2.1 Hz, 1H) 7.69-7.81 (m, 1H) 7.92 (dd, J=7.3, 2.0 Hz, 1H).

Co. No. 24: (400 MHz, DMSO-d$_6$) δ ppm 2.01 (t, J=18.97 Hz, 3H) 3.83 (d, J=14.13 Hz, 1H) 4.54 (d, J=14.13 Hz, 1H) 5.41 (br. s., 1H) 5.85 (br. s., 1H) 6.32 (t, J=3.43 Hz, 1H) 7.46 (br. s., 1H) 7.65 (dd, J=9.28, 2.42 Hz, 1H) 7.67-7.74 (m, 3H) 7.85 (d, J=807.00 Hz, 2H) 10.15 (br. s., 1H) 10.44 (br. s., 1H).

Co. No. 25: (400 MHz, CDCl$_3$) δ ppm 1.99 (t, J=18.4 Hz, 3H) 4.14 (br. s., 1H) 5.45 (br. s., 1H) 6.44-6.55 (m, 2H) 7.05-7.17 (m, 1H) 7.30 (d, J=2.0 Hz, 1H) 7.34 (t, J=2.3 Hz, 1H) 7.41 (d, J=2.0 Hz, 1H) 7.71-7.83 (m, 1H) 7.91 (dd, J=7.3, 2.3 Hz, 1H).

Co. No. 26: (400 MHz, CDCl$_3$) δ ppm 1.99 (t, J=18.3 Hz, 3H) 4.12 (br. s., 1H) 5.44 (br. s., 1H) 6.42-6.55 (m, 2H) 7.05 (dd, J=8.9, 2.4 Hz, 1H) 7.09-7.20 (m, 1H) 7.33 (t, J=2.1 Hz, 1H) 7.72-7.83 (m, 1H) 7.92 (dd, J=7.3, 2.3 Hz, 1H).

Co. No. 27: (400 MHz, CDCl$_3$) δ ppm 1.92 (t, J=18.2 Hz, 3H) 4.16 (br. s., 1H) 5.47 (br. s., 1H) 6.42-6.55 (m, 2H) 7.04 (dd, J=8.9, 2.4 Hz, 1H) 7.16 (dd, J=8.3, 2.5 Hz, 1H) 7.29-7.36 (m, 1H) 7.51 (m, J=8.3 Hz, 2H) 7.76 (m, J=8.0 Hz, 2H).

Co. No. 28: (300 MHz, CDCl$_3$) δ ppm 1.91 (t, J=18.2 Hz, 3H) 2.59 (s, 3H) 4.04 (d, J=11.1 Hz, 1H) 5.11 (d, J=11.1 Hz, 1H) 6.33-6.44 (m, 1H) 6.44-6.53 (m, 1H) 7.12 (d, J=8.3 Hz, 1H) 7.33 (d, J=8.1 Hz, 1H) 7.45-7.58 (m, 3H) 7.84 (d, J=8.1 Hz, 2H).

Co. No. 29: (300 MHz, CDCl$_3$) δ ppm 2.00 (t, J=18.9 Hz, 3H) 4.20 (br. s., 1H) 5.53 (br. s., 1H) 6.42-6.50 (m, 1H) 6.50-6.56 (m, 1H) 7.28-7.35 (m, 2H) 7.37 (dd, J=2.8, 1.7 Hz, 1H) 7.38-7.43 (m, 1H) 7.46-7.63 (m, 3H).

Co. No. 30: (400 MHz, CDCl$_3$) δ ppm 2.00 (t, J=18.6 Hz, 3H) 4.73 (br. s., 2H) 6.42-6.49 (m, 1H) 6.50-6.57 (m, 1H) 7.09 (t, J=8.5 Hz, 1H) 7.18 (d, J=8.0 Hz, 1H) 7.31-7.41 (m, 2H) 7.47-7.61 (m, 3H).

Co. No. 31: (400 MHz, CDCl$_3$) δ ppm 2.00 (t, J=18.4 Hz, 3H) 4.14 (br. s., 1H) 5.48 (br. s., 1H) 6.44-6.51 (m, 1H) 6.51-6.59 (m, 1H) 7.04 (dd, J=8.9, 2.4 Hz, 1H) 7.17 (dd, J=8.3, 2.3 Hz, 1H) 7.34 (dd, J=2.8, 1.5 Hz, 1H) 7.54 (d, J=3.3 Hz, 3H).

Co. No. 32: (300 MHz, CDCl$_3$) δ ppm 1.92 (t, J=18.1 Hz, 3H) 4.70 (br. s., 2H) 6.43-6.55 (m, 2H) 7.11 (dd, J=8.6, 1.8 Hz, 1H) 7.18-7.23 (m, 1H) 7.31-7.39 (m, 1H) 7.51 (m, J=8.3 Hz, 2H) 7.74 (m, J=8.1 Hz, 2H).

Co. No. 33: (400 MHz, DMSO-d$_6$) δ ppm 2.02 (t, J=18.97 Hz, 3H) 4.57 (br. s., 2H) 6.55 (t, J=3.23 Hz, 1H) 6.59 (dd, J=3.84, 1.41 Hz, 1H) 7.36 (td, J=9.49, 2.42 Hz, 1H) 7.40-7.48 (m, 1H) 7.51-7.58 (m, 2H) 7.62 (t, J=7.87 Hz, 1H) 7.81 (dd, J=2.62, 1.41 Hz, 1H).

Co. No. 34: (400 MHz, CDCl$_3$) δ ppm 1.88-2.10 (m, 3H) 4.42 (br. s., 1H) 4.78 (br. s., 1H) 6.45-6.50 (m, 2H) 7.12 (dd, J=10.0, 8.8 Hz, 1H) 7.29 (dd, J=8.0, 2.0 Hz, 1H) 7.36 (t, J=2.3 Hz, 1H) 7.40 (d, J=2.0 Hz, 1H) 7.42 (d, J=8.0 Hz, 1H) 7.69-7.79 (m, 1H) 7.93 (dd, J=7.4, 2.1 Hz, 1H).

Co. No. 35: (400 MHz, CDCl$_3$) δ ppm 1.93-2.06 (m, 3H) 4.27 (d, J=11.3 Hz, 1H) 4.86 (d, J=11.0 Hz, 1H) 6.39-6.45 (m, 1H) 6.49 (dd, J=3.6, 1.4 Hz, 1H) 7.13 (dd, J=10.2, 8.9 Hz, 1H) 7.24 (t, J=8.0 Hz, 1H) 7.41-7.46 (m, 1H) 7.48 (dd, J=8.2, 1.4 Hz, 1H) 7.59 (dd, J=2.6, 1.4 Hz, 1H) 7.79-7.89 (m, 1H) 8.03 (dd, J=7.3, 2.3 Hz, 1H).

D. Pharmacological Examples

Example D.1

Measurement of Antifungal Activity In Vitro

The standard susceptibility screen was performed in 96-well plates (U-bottom, Greiner Bio-One). Serial dilutions (2-fold or 4-fold) of 20 mM compound stock solutions were made in 100% DMSO, followed by an intermediate dilution step in water. These serial dilutions (10 µl) were then spotted onto test-plates that could be stored in the dark at 4° C. for a maximum period of 2 weeks. An adequate broad dose-range was included with 64 µM as the highest in-test concentration. The culture medium RPMI-1640 was supplemented with L-glutamine, 2% glucose and buffered with 3-(N-morpholino)-propanesulfonic acid (MOPS) at pH 7.0±0.1.

The different fungal species/isolates (Table 3a) were cryopreserved and 1/1000 diluted in medium just prior to use. A standard inoculum of 200 µl containing $10^3$ colony-forming unit (cfu) was then added to each well. A positive control (100% growth=fungal culture without antifungal) and a negative control (0% growth=RPMI-MOPS medium) were included on each plate. Optimal incubation time and temperature were dependent on the fungal species and vary from 24 h for yeasts (37° C.) to one week or more for dermatophytes (27° C.). Inhibition of fungal growth was measured after adding 10 µl of 0.005% (w/v) resazurin (Sigma Aldrich) to each well, based on the principle that living cells convert the non-fluorescent blue resazurin into the pink and fluorescent resorufin, allowing fluorimetric reading (λhd ex 550 nm and µ$_{em}$ 590 nm) after an additional incubation period ('resa' time mentioned in Table 3a). Results are shown in Table 3b as pIC$_{50}$ values.

TABLE 3a

Incubation conditions for the different fungal species. 'Resa time' represents the additional incubation time after the addition of resazurin to the test system.

| Species | Temperature (° C.) | Time | Resa time |
| --- | --- | --- | --- |
| Microsporum canis | 27 | 9 days | 24 hours |
| Trichophyton mentagrophytes | 27 | 7 days | 24 hours |

TABLE 3a-continued

Incubation conditions for the different fungal species. 'Resa time' represents the additional incubation time after the addition of resazurin to the test system.

| Species | Temperature (° C.) | Time | Resa time |
|---|---|---|---|
| Trichophyton rubrum | 27 | 7 days | 24 hours |
| Scedosporium apiospermum | 37 | 48 hours | 17 hours |
| Scedosporium prolificans | 37 | 48 hours | 17 hours |
| Sporothrix schenkii | 27 | 4 days | 24 hours |
| Aspergillus fumigatus | 27 | 48 hours | 17 hours |
| Candida parapsilosis | 37 | 24 hours | 4 hours |
| Cryptococcus neoformans | 37 | 24 hours | 4 hours |
| Rhizopus oryzae | 37 | 24 hours | 6 hours |
| Rhizomucor miehei | 37 | 48 hours | 17 hours |
| Mucor circinelloides | 27 | 48 hours | 17 hours |

TABLE 3b

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 1 | 4.68 | 6.45 | 6.91 | 5.70 | 6.72 | 5.30 | 6.89 | <4.19 | n.d. | <4.19 | <4.19 |
| 5 | <4.19 | <4.19 | 4.22 | <4.19 | <4.19 | 4.46 | <4.19 | n.d. | n.d. | n.d. | n.d. |
| 6 | 5.58 | 4.76 | 5.23 | <4.19 | 6.03 | 5.85 | 5.61 | <4.19 | <4.19 | <4.19 | <4.19 |
| 7 | <4.19 | 5.40 | 5.40 | <4.19 | <4.19 | <4.19 | <4.19 | n.d. | n.d. | n.d. | n.d. |
| 8 | <4.19 | 5.40 | 5.52 | <4.19 | <4.19 | <4.19 | 4.22 | n.d. | n.d. | n.d. | n.d. |
| 9 | 4.96 | 5.40 | 6.00 | <4.19 | 5.10 | 6.06 | 4.89 | 5.02 | 5.22 | <4.19 | <4.19 |
| 10 | <4.19 | <4.19 | <4.19 | <4.19 | <4.19 | <4.19 | <4.19 | n.d. | n.d. | n.d. | n.d. |
| 11 | <4.19 | <4.19 | 4.86 | <4.19 | <4.19 | <4.19 | <4.19 | n.d. | n.d. | n.d. | n.d. |
| 13 | <4.19 | 4.23 | 5.70 | <4.19 | 4.81 | <4.19 | 5.14 | n.d. | n.d. | n.d. | n.d. |
| 4 | 4.92 | 6.32 | 6.63 | 5.51 | 5.65 | 4.67 | 6.05 | <4.19 | 6.83 | <4.19 | <4.19 |
| 14 | 4.36 | 6.28 | 6.43 | 5.52 | 5.70 | 4.43 | 6.22 | 5.76 | 5.88 | <4.19 | 4.34 |
| 15 | <4.19 | 6.31 | 7.37 | 6.20 | 6.65 | <4.19 | 6.60 | <4.19 | 5.60 | 4.47 | <4.19 |
| 2 | <4.19 | 5.09 | 5.82 | <4.19 | <4.19 | <4.19 | 5.43 | n.d. | n.d. | n.d. | n.d. |
| 3 | <4.19 | 6.30 | 6.96 | 5.58 | 5.70 | 5.26 | 6.36 | 5.13 | 6.15 | <4.19 | 4.59 |
| 16 | 5.42 | 5.70 | 6.21 | 4.97 | 5.77 | 6.14 | 5.78 | 4.99 | 5.92 | <4.19 | <4.19 |
| 17 | 5.25 | 5.58 | 6.34 | 5.61 | 6.26 | 6.49 | 5.79 | <4.19 | 6.12 | 5.08 | <4.19 |
| 18 | 5.09 | 5.67 | 6.83 | 5.63 | 6.30 | 5.79 | 5.96 | <4.19 | 6.10 | <4.19 | 4.30 |
| 19 | 5.55 | 5.69 | 6.67 | 4.88 | 5.69 | 5.79 | 6.19 | 5.63 | 6.29 | 5.01 | 4.84 |
| 20 | <4.19 | 6.29 | 6.84 | 4.89 | 6.95 | <4.19 | 6.10 | 6.24 | 6.80 | <4.19 | 4.57 |
| 21 | 5.43 | 6.32 | 6.71 | 5.61 | 6.90 | 5.80 | 6.16 | 7.05 | 7.30 | <4.19 | 5.18 |
| 22 | <4.19 | 5.11 | 5.11 | <4.19 | <4.19 | <4.19 | <4.19 | n.d. | n.d. | n.d. | n.d. |
| 23 | 5.02 | 6.38 | 6.89 | 5.44 | 6.27 | <4.19 | 6.10 | 6.74 | 7.00 | <4.19 | <4.19 |
| 24 | <4.19 | 5.11 | 6.21 | 5.58 | 4.94 | <4.19 | 5.77 | n.d. | n.d. | n.d. | n.d. |
| 25 | 4.85 | 5.80 | 5.90 | <4.19 | 5.99 | <4.19 | 5.66 | 6.39 | 6.30 | <4.19 | <4.19 |
| 26 | 4.99 | 6.33 | 6.33 | 5.42 | 6.23 | <4.19 | 5.92 | 6.80 | 6.72 | <4.19 | 4.87 |
| 27 | 5.61 | 6.29 | 6.54 | 5.74 | 6.30 | 5.99 | 5.82 | 6.36 | 7.00 | <4.19 | 5.08 |
| 28 | 4.55 | 4.85 | 5.13 | 4.34 | 4.19 | 4.78 | 4.57 | 6.15 | 5.64 | <4.19 | 4.38 |
| 29 | <4.19 | 6.96 | 7.07 | <4.19 | 6.30 | <4.19 | 6.72 | <4.19 | <4.19 | <4.19 | <4.19 |
| 30 | <4.19 | 6.33 | 6.79 | 5.11 | 6.30 | 5.85 | 6.44 | 5.05 | 5.34 | <4.19 | 4.91 |
| 31 | 5.63 | 6.36 | 6.33 | 5.46 | 6.30 | 6.53 | 5.90 | 4.98 | 5.06 | <4.19 | <4.19 |
| 32 | 5.21 | 5.78 | 5.78 | 5.56 | 5.70 | 5.89 | 5.78 | <4.19 | <4.19 | <4.19 | <4.19 |
| 33 | 5.03 | 5.71 | 6.14 | 4.87 | 5.72 | 5.58 | 5.67 | 6.19 | 4.98 | <4.19 | <4.19 |
| 34 | 5.10 | 5.09 | 5.10 | 5.53 | 5.10 | 5.24 | 5.09 | n.d. | n.d. | n.d. | n.d. |
| 35 | 5.37 | 6.28 | 6.52 | 4.83 | 5.84 | 6.28 | 5.80 | n.d. | n.d. | n.d. | n.d. |
| 12 | n.d. | n.d. | n.d. | n.d. | n.d. | n.d. | n.d. | n.d. | n.d. | n.d. | n.d. |

The $pIC_{50}$ values for Inf. 'L' were determined for compounds 1, 3, 4, 6, 9, 14-21, 23, 25-33, and were <4.19.
('n.d.' means not determined; 'Inf.' means infection; values are $pIC_{50}$ values)
Inf. 'A': *Sporothrix schenkii* B62482
Inf. 'B': *Microsporum canis* B68128
Inf. 'C': *Trichophyton rubrum* B68183
Inf. 'D': *Candida parapsilosis* B66126
Inf. 'E': *Aspergillus fumigatus* B42928
Inf. 'F': *Cryptococcus neoformans* B66663
Inf. 'G': *Trichophyton mentagrophytes* B70554
Inf. 'H': *Scedosporium apiospermum* IHEM3817
Inf. 'I': *Scedosporium prolificans* IHEM21157
Inf. 'J': *Rhizopus oryzae* IHEM5223
Inf. 'K': *Rhizomucor miehei* IHEM13391
Inf. 'L': *Mucor circinelloides* IHEM21105

Example D.2

Solubility

'UPLC' means Ultra Performance Liquid Chromatography; 'HPBCD' means 2-hydroxypropyl-β-cyclodextrin.

An amount of the compound to be tested, typically between 2 mg and 4 mg, was accurately weighed using a microbalance and added to 0.5 ml of one of the buffer systems below in a 20 ml clear glass vial:
A) 0.01 N HCl
B) buffer pH 4: phosphate (0.2 M)—citrate mixture (0.1 N) in accordance to Mc Ilvaine's buffer solutions)
C) buffer pH 4, containing 10% (w/v) of HPBCD
D) buffer pH 4, containing 20% (w/v) of HPBCD
E) buffer pH 7.4: phosphate (0.2 M)—citrate mixture (0.1 N) in accordance to Mc Ilvaine's buffer solutions)

F) buffer pH 7.4, containing 10% (w/v) of HPBCD
G) buffer pH 7.4, containing 20% (w/v) of HPBCD A magnetic stirring bar was added to the mixtures. The mixtures were stirred at ambient temperature for at least 2 hours and then visually inspected.

If the compound was dissolved, the result was reported (twice the weighed amount of compound/ml).

If the compound was not dissolved, 0.5 ml of extra solvent was added to the suspension. The mixtures were stirred at ambient temperature for at least another 2 hours, followed by inspection.

If the compound was dissolved, the result was reported (weighed amount of compound/ml).

If the compound was not dissolved, 1 ml of extra solvent is pipetted into the suspension. The mixtures were shaken (Edmund Buhler SM25 175 SPM) at ambient temperature overnight and inspected afterwards.

If the compound was dissolved, the result was reported (half the weighed amount of compound/ml).

If the compound was not dissolved, the suspension was filtered over a filter disc. An aliquot of the filtrate was diluted with an appropriate solvent (0.1 N HCl/acetonitrile 1/1) and submitted for concentration measurement (mg/ml) using a generic UPLC method.

The animals were dosed orally by gastric intubation at 10 ml/kg to obtain a final dose 10 mg/kg. Three dosed animals were sacrificed for blood sampling at 15 and 30 min, 1, 2, 3, 4, 6, 8 and 24 h after PO dose administration as a solution and at 30 min, 1, 2, 4, 6, 8 and 24 h after PO dose administration as a suspension.

Blood was collected by multiple sampling from a tail vein into Multivette® 600 K3E tubes (Sarstedt). Samples were placed immediately at approximately 4° C. and plasma was obtained following centrifugation at 4° C. for 10 minutes at approximately 1900×g. All samples were shielded from daylight and stored at ≤−18° C. prior to analysis.

Plasma samples were analysed for dosed compound using a qualified research LC-MS/MS method. The key analytical performance (linearity, upper and lower limit of quantification, accuracy and precision) of the method was reported together with the plasma concentrations.

A limited pharmacokinetic analysis was performed using WinNonlin™ Professional (Version 5.2.1). A non-compartmental analysis using the lin/log trapezoidal rule with lin/log interpolation was used for all data.

TABLE 4

| Buffer system | Compound 23 of WO02/34752 UPLC (mg/ml) | Compound 17 of the present invention UPLC (mg/ml) |
| --- | --- | --- |
| A | 1.878 | 7.10 > X > 3.55 |
| B | <0.001 | 0.087 |
| C | 0.048 | 1.229 |
| D | 1.49 | n.d. |
| E | <0.001 | <0.001 |
| F | 0.035 | 0.191 |
| G | 0.11 | 0.603 |

Example D.3

In Vivo Pharmacokinetic Determinations (Bioavailability)

Three animals (mean weight 20±7 g for mice and 275±20 for Guinea pigs) were used per dose route, time point and formulation.

For the oral (PO) solution formulation, compound was dissolved in a 20% hydroxypropyl-β-cyclodextrin (HP-β-CD) solution at a final concentration of 1 mg/ml. HCl was added to facilitate dissolution. After dissolution, the pH was brought up to 3.7 with NaOH. Mannitol was added to make the solution isotonic. For the PO suspension formulation, compound was suspended in 0.5% methocel at a final concentration of 1 mg/ml. The formulations were stored at room temperature, protected from light and analysed quantitatively with LC-MS/MS on the day of preparation. Stability of the formulations was checked on the day of dosing.

TABLE 5

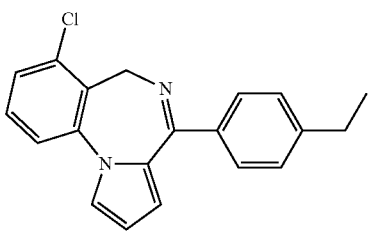 [SMILES: CCc1ccc(C2=NCc3c(Cl)cccc3-n3cccc32)cc1]

Compound 22 of WO02/34752
Bioavailability in mice: 11% (PO 10 mg/kg; IV 2.5 mg/kg)
Bioavailability in guinea pigs: 2.7%(PO 40 mg/kg; IV 2.5 mg/kg)

TABLE 5-continued

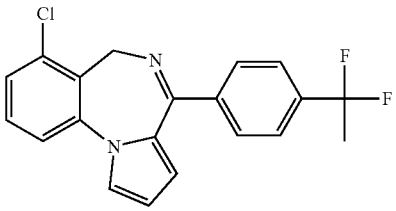 [SMILES: CC(F)(F)c1ccc(C2=NCc3c(Cl)cccc3-n3cccc32)cc1]

Compound 4 of the present application
Bioavailability in mice: 20% (PO 10 mg/kg; IV 2.5 mg/kg)
Bioavailability in guinea pigs: 35% (PO 10 mg/kg; IV 1.25 mg/kg)

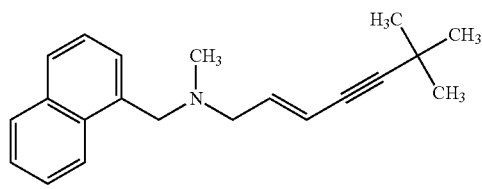 [SMILES: CN(C/C=C/C#CC(C)(C)C)Cc1cccc2ccccc12]

Terbinafine
Bioavailability in mice: 19% (PO 10 mg/kg; IV 2.5 mg/kg)
Bioavailability in guinea pigs: 14% (PO 10 mg/kg; IV 2.5 mg/kg)

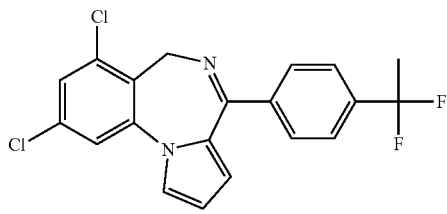 [SMILES: CC(F)(F)c1ccc(C2=NCc3c(Cl)cc(Cl)cc3-n3cccc32)cc1]

Compound 9 of the present application
Bioavailability in mice: 100% (PO 20 mg/kg; IV 2.5 mg/kg)
Bioavailability in guinea pigs: not soluble enough

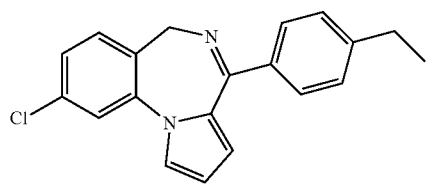 [SMILES: CCc1ccc(C2=NCc3ccc(Cl)cc3-n3cccc32)cc1]

Compound 23 of WO02/34752
Bioavailability in guinea pigs: 7% (PO 40 mg/kg; IV 2.5 mg/kg)

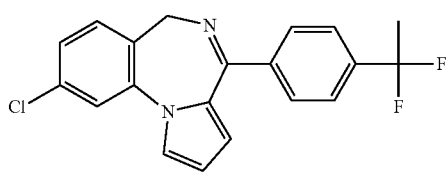 [SMILES: CC(F)(F)c1ccc(C2=NCc3ccc(Cl)cc3-n3cccc32)cc1]

Compound 17 of the present application
Bioavailability in guinea pigs: 70% (PO 10 mg/kg; IV 2.5 mg/kg)

Example D.4

Measurement of Antifungal Activity In Vivo

General

The animals used in the tests described below were female Guinea pigs (Duncan-Hartley, Charles River, 200 g). These animals were kept in groups of 2 or 3 in cages of 56×33×20 cm$^3$. Food pellets (Carfil Quality) and water were available ad libitum in addition to a small daily amount of hay. Standard husbandry conditions were adopted: room temperature: 22° C., humidity level: 60% and a day-night cycle of 12 h.

For the preparation of inoculums, *Microsporum canis* (strain B68128) was grown on Sabouraud Dextrose Agar (SDA) plates for at least one week (7-10 days) before infection (27° C.). On the day of infection, spores were harvested by adding 4-5 ml sterile water on the plate and suspending the infectious material with a bend Pasteur pipette. From the recollected fluid, 10 µl was added to a KOVA counting chamber for determination of the number of spores in 1 square (average of several squares). If needed, additional dilutions (10× or 100×) were prepared. The average number of spores in one square×dilution× 90.000=cfu/ml. An inoculum of 1×10$^7$ cfu/ml was prepared in a honey-water mixture (50%-50%).

In the tests described below, semi-quantitative lesion scores were given based on different clinical parameters. Scores between 0 and 3.5 were assigned based on the severity and size of the lesion. The criteria are listed in detail in Table 6.

TABLE 6

Criteria for the semi-quantitative dermal lesion scores

| Type of lesion | <0.5 cm | 0.5-1.5 cm | 1.5-3 cm | >3cm |
| --- | --- | --- | --- | --- |
| only scarification lesion or no lesion | 0 | 0 | 0 | 0 |
| erythema | 0 | 0.5 | 1 | 1.5 |
| pilo-erection | 0 | 0.5 | 1 | 1.5 |
| thin white scales (separate) | 0.5 | 1.5 | 2 | 2.5 |
| thick white crusts (1 larger crust) | 1 | 2 | 2.5 | 3 |
| erosion/red crusts | 1.5 | 2.5 | 3 | 3.5 |
| no more crusts, alopecia, irregular skin | 0.5 | 0.5 | 1 | 1.5 |
| irregular skin, without alopecia | 0.5 | 0.5 | 0.5 | 1 |
| smooth skin (alopecia or not) | 0 | 0 | 0 | 0 |

Test D.4.1

Activity of Compound 4 and Compound 14 Against *M. canis* in Guinea-Pigs after Oral Treatment at Different Dosages for 7 Consecutive Days Artificial Infection Procedure The dorsum of the guinea pigs was shaved and further depilated for 3 minutes with Veet® creme before scarification with a steel brush. An inoculum of 10$^6$ cfu in 150 µl (75 mQ+75 µl honey) was applied to the wound using a micropipette with disposable tips. The animal was kept immobilized until the inoculum had completely dried.

Formulations vehicle: methocel 0.5%, Tween 80® (polysorbate 80), demineralised water reference compound: itraconazole at 6.25 mg/ml test compounds: prepared at 25 mg/ml, subsequently further diluted Dosing and Experimental Groups Oral treatment (gavage 0.16 ml/100 g once daily) was started about 2 hours before infection and continued once daily for 7 consecutive days. The animals were weighed after 3 days of treatment to adjust for the dose.

| G1: Vehicle-treated infected control (VIC) | (2 animals) |
|---|---|
| G2: Terbinafine (10 mg/kg) | (mean value of large number of experiments) |
| G3: Itraconazole (10 mg/kg) | (2 animals) |
| G4: Compound 4 (40 mg/kg) | (2 animals) |
| G5: Compound 4 (10 mg/kg) | (3 animals) |
| G6: Compound 4 (5 mg/kg) | (3 animals) |
| G7: Compound 14 (40 mg/kg) | (3 animals) |
| G8: Compound 14 (20 mg/kg) | (3 animals) |
| G9: Compound 14 (10 mg/kg) | (3 animals) |

Monitoring of Infection

Developments of lesions were evaluated following the semi-quantitative lesion scoring system (see Table 6) on days 3, 5, 7, 10, 12, 14, 17 and 20. The results are show in Table 7 ("DPI" means days post infection). Reported values in Table 7 are mean values.

TABLE 7

| DPI | G1 | G2 | G3 | G4 | G5 | G6 | G7 | G8 | G9 |
|---|---|---|---|---|---|---|---|---|---|
| 3 | 0 | 0 | 0 | 0 | 0 | 0 | 0 | 0 | 0.33 |
| 5 | 1.00 | 0 | 0 | 0.17 | 0 | 0.67 | 0.17 | 0.33 | 1.17 |
| 7 | 2.00 | 0.08 | 0 | 0.17 | 0.33 | 1.50 | 0.67 | 0.83 | 2.00 |
| 10 | 2.25 | 0.33 | 0 | 0.17 | 1.00 | 2.00 | 1.17 | 1.67 | 2.17 |
| 12 | 2.75 | 0.80 | 0 | 0.17 | 1.50 | 2.17 | 0.83 | 2.00 | 2.33 |
| 14 | 1.75 | 0.75 | 0 | 0 | 1.50 | 1.83 | 0.50 | 1.67 | 2.17 |
| 17 | 1.00 | 0.50 | 0 | 0.17 | 0.50 | 1.33 | 0.17 | 1.50 | 1.67 |
| 20 | 0.75 | 0.42 | 0 | 0.17 | 0.33 | 1.17 | 0.17 | 0.67 | 1.17 |

From Table 7, can be concluded that the vehicle-treated infected controls (G1) developed a normal course of infection, i.e. first lesions after about 5 days with a maximal severity around day 12. Both guinea pigs still showed some white scales at the end of the experiment (day 20).

The animals treated with itraconazole (10 mg/kg) (G3) never developed any lesions. As for the test compounds, a clear dose-response was seen. Compound 4 is, at 40 mg/kg) (G4), remarkably more active than the terbinafine group (G2). The activity of groups G5 and G7 are comparable to G2.

For the sake of comparison, 2 compounds not having the 1,1-difluoroethyl moiety in the $R^5$ or $R^6$ position, were tested in an analogous protocol:

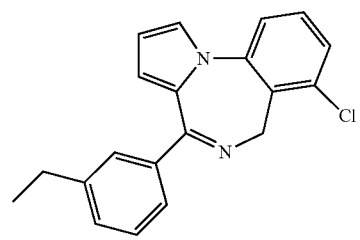

derivative of compound 14
G10: 50 mg/kg

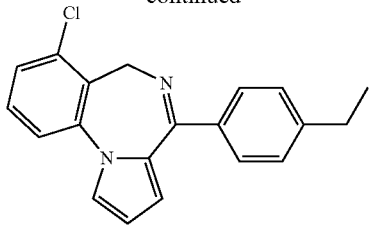

Compound 22 of WO02/34752
derivative of compound 4
G11: 50 mg/kg

Artificial Infection Procedure

The dorsum of the guinea pigs was shaved and further depilated for 7 minutes with Veet® creme before scarification with a steel brush. An inoculum of $10^6$ cfu in 200 µl (100 µl mQ+100 µl honey) was applied to the wound using a micropipette with disposable tips. The animal was kept immobilized until the inoculum had completely dried.

Formulations

Vehicle: methocel F4M Premium EP, Tween 80® (polysorbate 80), demineralised water.

Test compounds: prepared at 30 mg/ml, subsequently further diluted until 6 mg/ml.

Dosing and Experimental Groups

Oral treatment (gavage 0.40 ml/guinea pig once daily) was started about 2 hours before infection and continued once daily for 7 consecutive days.

Monitoring of Infection

Developments of lesions were evaluated following the semi-quantitative lesion scoring system (see Table 6) on days 3, 5, 7, 10, 12, 14, 18 and 21. The results are show in Table 8. Reported values in Table 8 are mean values.

TABLE 8

| DPI | G10 | G11 |
|---|---|---|
| 3 | 0 | 0 |
| 5 | 0.5 | 0 |
| 7 | 1 | 0.5 |
| 10 | 1 | 0.5 |
| 12 | 2 | 0.5 |
| 14 | 1 | 1 |
| 18 | 1 | 0.5 |
| 21 | 0.5 | 0.5 |

The compounds used in G10 and G11 showed partial activity. However even at a higher dose (50 mg/kg), the compounds used in G10 and G11 turned out to be less active than present compounds 14 and 4 used in G7 and G4 (both at 40 mg/kg).

Example D.5

Squalene-Epoxidase Inhibition

Using subcellular fractions of *Candida albicans*, a method was developed enabling to quantify the effects of chemical compounds on different steps in the ergosterol biosynthesis.

*C. albicans*, strain B2630, was grown for 24 hours (h) in a 500 ml Erlenmeyer flask containing 100 ml CYG medium (0.5% casein hydrolysate, 0.5% yeast extract and 0.5% glucose) at 37° C. aerobically in a rotating shaker. After this incubation period, 1 ml aliquots were used to inoculate another 100 ml CYG medium. Cells were grown as above for 8 h. 5 ml of this 8 h-culture was used to inoculate 200 ml PYG medium (1% polypeptone, 1% yeast extract and 4% glucose) in a 500 ml Erlenmeyer flask. Cells were grown at 30° C. for 8 h as a standing culture and for another 8 h in a rotating shaker at 100 rpm.

After incubation, the yeast cells were collected by centrifugation (5 min at 1500 g) and washed twice with ice cold physiological saline. The cells were resuspended in 15 ml homogenization buffer (30 mM nicotinamide, 5 mM $MgCl_2$ and 5 mM reduced glutathione in 100 mM potassium phosphate buffer pH 7.4) and brought into an ice cold 80 ml Bead-Beater recipient containing 40 ml glass beads. The outer jacket of the Bead-Beater was filled with ice-cold water. Cells were homogenized for 3 times 1 min with intermitting cooling. The homogenate was centrifuged at 4° C. for 20 min at 8000 g. Protein concentration of the 8000 g supernatant was measured by the Bio-Rad method. The Bio-rad method is a rapid protein measurement. It is a dye-binding assay based on the differential color change of a dye in response to various concentrations of protein based on the method of Bradford. In a typical assay 0.1 ml properly diluted sample was mixed with 5.0 ml dye reagent. A blue-green color resulted which was read by a spectrophotometer at 595 nm. A standard curve was prepared using 10-150 micrograms gamma globulin.

$^{14}C$ mevalonate incorporation was measured in a reaction mixture containing in a final volume of 1 ml: 900 µl S8000 fraction (protein 4 mg/ml), 3 mM $MgCl_2$, 2 mM $MnCl_2$, 5.4 mM ATP, 1.38 mM NADH, 1.51 mM NADPH, 0.3 µCi $^{14}C$-mevalonate and 10 µl drug and/or solvent. After an incubation period of 2 h at 30° C. in a reciprocating shaker at 120 spm (scintillations per minute), the reaction was stopped by the addition of 1 ml 15% KOH in 90% ethanol. After saponification for 1 h at 80° C. and cooling, non-saponifiable lipids were extracted with 3 ml n-heptane and the extracts dried under a stream of nitrogen. Lipids were separated by TLC (Silicagel $60F_{254}$, Merck) using a solvent system consisting of 75 volumes HIA (n-heptaan/di-iospropylether/acetic acid, 60/40/4, v/v/v) and 25 volumes ethyl acetate. Lipid fraction were visualized by phosphor-imaging, scanned with a Typhoon 9200 Variabel Mode Imager and quantified using the ImageQuant 5.0 software. Using the above described method, 14α-demethylase as well as squalene-epoxidase as Δ14 reductase- and the Δ7-Δ8 isomerase inhibitors could be detected.

By following the protocol described hereabove, it was determined that the compounds according to Formula(I) are squalene epoxidase inhibitors.

E. Composition Example

"Active ingredient" as used throughout these examples, relates to a compound of Formula (I), including any stereochemically isomeric form thereof, a pharmaceutically acceptable salt thereof or a solvate thereof; in particular to any one of the exemplified compounds.

Example E1

Injectable Solution 1.8 Grams methyl 4-hydroxybenzoate and 0.2 grams sodium hydroxide were dissolved in about 0.5 l of boiling water for injection. After cooling to about 50° C. there were added while stirring 0.05 grams propylene glycol and 4 grams of the active ingredient. The solution was cooled to room temperature and supplemented with water for injection q.s. ad 1 l, giving a solution comprising 4 mg/ml of active ingredient. The solution was sterilized by filtration and filled in sterile containers.

Example E2

Transungual Composition 0.144 g $KH_2PO_4$, 9 g NaCl, 0.528 g $Na_2HPO_4.2H_2O$ was added to 800 ml $H_2O$ and the mixture was stirred. The pH was adjusted to 7.4 with NaOH and 500 mg $NaN_3$ was added. Ethanol (42 v/v %) was added and the pH was adjusted to 2.3 with HCl. 15 mg active ingredient was added to 2.25 ml PBS (Phosphate Buffer Saline)/Ethanol (42%; pH 2.3) and the mixture was stirred and treated with ultrasound. 0.25 ml PBS/Ethanol (42%; pH 2.3) was added and the mixture was further stirred and treated with ultrasound until all active ingredient was dissolved, yielding the desired transungual composition.

Example E3

Oral Drops

500 Grams of the A.I. was dissolved in 0.5 l of a sodium hydroxide solution and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example E4

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example E5

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example E6

2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a separately prepared mixture of purified water, propylene glycol (200 mg) and polysorbate 60 (15 mg) having a temperature of 70 to 75° C. while using a homogenizer for liquids. The resulting mixture is allowed to cool to below 25° C. while continuously mixing. A solution of A.I. (20 mg), polysorbate 80 (1 mg) and purified water q.s. ad 1 g and a solution of sodium sulfite anhydrous (2 mg) in purified water are next added to the emulsion while continuously mixing. The cream is homogenized and filled into suitable tubes.

Example E7

2% Cream

A mixture of A.I. (2 g), phosphatidyl choline (20 g), cholesterol (5 g) and ethyl alcohol (10 g) is stirred and heated at 55-60° C. until complete solution and is added to a solution of methyl paraben (0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

The invention claimed is:
1. A compound of Formula (I)

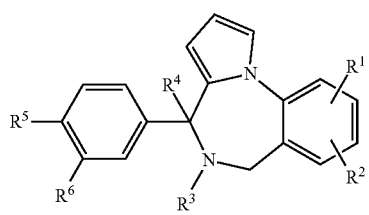

(I)

or a stereoisomeric form thereof, wherein
$R^1$ is hydrogen, chloro or fluoro;
$R^2$ is hydrogen, chloro, fluoro or methyl;
$R^3$ and $R^4$ are hydrogen;
or $R^3$ and $R^4$ taken together form a bond;
$R^5$ is 1,1-difluoroethyl, and $R^6$ is hydrogen or fluoro;
or $R^5$ is hydrogen or fluoro, and $R^6$ is 1,1-difluoroethyl;
or a pharmaceutically acceptable addition salt or a solvate thereof.

2. The compound according to claim 1, wherein $R^1$ is chloro or fluoro.

3. The compound according to claim 1, wherein $R^1$ is chloro or fluoro; and wherein
$R^2$ is chloro, fluoro or methyl.

4. The compound according to claim 1, wherein
$R^1$ is chloro or fluoro;
$R^2$ is hydrogen, chloro, fluoro or methyl;
$R^3$ and $R^4$ are taken together to form a bond;
$R^5$ is 1,1-difluoroethyl, and $R^6$ is hydrogen or fluoro;
or $R^5$ is hydrogen or fluoro, and $R^6$ is 1,1-difluoroethyl.

5. The compound according to claim 1, wherein
$R^1$ is chloro or fluoro;
$R^2$ is hydrogen;
$R^3$ and $R^4$ taken together form a bond;
$R^5$ is 1,1-difluoroethyl;
$R^6$ is hydrogen.

6. The compound according to claim 1, wherein
$R^1$ is in the 7-position and is chloro or fluoro; and
$R^2$ is in any of the other positions and is hydrogen, chloro, fluoro or methyl.

7. The compound according to claim 1, wherein the compound is 7-chloro-4-[4-(1,1-difluoroethyl)phenyl]-6H-pyrrolo[1,2-a][1,4]benzodiazepine.

8. A pharmaceutical composition comprising a pharmaceutically acceptable carrier and, as active ingredient, a therapeutically effective amount of a compound as defined in any one of claims 1 to 7.

9. A compound as defined in any one of claims 1 to 7 for use as a medicament.

10. A compound as defined in any one of claims 1 to 7 for use in the treatment or prevention of a fungal infection.

11. The compound for use according to claim 10 wherein the fungal infection is caused by one or more of the fungi selected from the group consisting of *Candida* spp.; *Aspergillus* spp.; *Cryptococcus neoformans*; *Sporothrix schenckii*; *Epidermophyton floccosum*; *Microsporum* spp.; *Trichophyton* spp; *Fusarium* spp.; *Rhizomucor* spp.; *Mucor circinelloides*; *Rhizopus* spp.; *Malassezia furfur*; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*.

12. The compound for use according to claim 10 wherein the fungal infection is caused by one or more of the fungi selected from the group consisting of *Candida parapsilosis*; *Aspergillus* spp.; *Cryptococcus neoformans*; *Sporothrix schenckii*; *Epidermophyton floccosum*; *Microsporum* spp.; *Trichophyton* spp.; *Fusarium* spp.; *Rhizomucor* spp.; *Mucor circinelloides*; *Rhizopus* spp.; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*.

13. The compound for use according to claim 10 wherein the fungal infection is caused by one or more of the fungi selected from the group consisting of *Microsporum canis*, *Trichophyton mentagrophytes*, *Trichophyton rubrum* and *Aspergillus fumigatus*.

* * * * *